US006203822B1

(12) United States Patent
Schlesinger et al.

(10) Patent No.: US 6,203,822 B1
(45) Date of Patent: *Mar. 20, 2001

(54) GALLIUM-CONTAINING COMPOUNDS FOR THE TREATMENT OF INFECTIONS CAUSED BY INTRACELLULAR PATHOGENS AND PATHOGENS CAUSING CHRONIC PULMONARY INFECTION

(75) Inventors: Larry S. Schlesinger; Bradley E. Britigan, both of Iowa City, IA (US)

(73) Assignee: University of Iowa Research Foundation, Iowa City, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/707,248

(22) Filed: Sep. 3, 1996

(51) Int. Cl.$^7$ .......................... A61K 33/24; A61K 31/28; A61K 9/00; A61K 38/21

(52) U.S. Cl. .......................... 424/650; 424/43; 424/600; 424/450; 424/85.5; 514/6; 514/37; 514/253; 514/255; 514/354; 514/492; 514/669; 514/924

(58) Field of Search .................................... 424/650, 600, 424/43, 450, 85.5; 514/6, 37, 253, 255, 354, 492, 669, 924

(56) References Cited

U.S. PATENT DOCUMENTS

| | | | |
|---|---|---|---|
| 5,175,006 | * 12/1992 | Matkovic et al. | 424/650 |
| 5,525,598 | 6/1996 | Collery et al. | 514/187 |
| 5,700,487 | * 12/1997 | Gerber et al. | 424/650 |
| 5,747,482 | 5/1998 | Bernstein | 514/184 |
| 5,877,210 | 3/1999 | Schieven | 514/492 |
| 5,883,088 | 3/1999 | Bernstein | 514/184 |
| 6,066,628 | * 5/2000 | Stojiljkovic et al. | 514/185 |

FOREIGN PATENT DOCUMENTS

| | | |
|---|---|---|
| WO 92/04896 | 4/1992 | (WO) . |
| WO 92/17182 | 10/1992 | (WO) . |
| WO 93/02087 | 2/1993 | (WO) . |
| WO 94/12192 | 6/1994 | (WO) . |
| WO 96/36331 | 11/1996 | (WO) . |
| WO 96/40108 | 12/1996 | (WO) . |

OTHER PUBLICATIONS

Chemical Abstracts 79: 122276 (1973).*
Chemical Abstracts 89: 141068 (1978).*
Chemical Abstracts 79: 122497 (1973).*
Chemical Abstracts 109: 236917 (1988).*
Bouissou et al., "Effect of gallium sulfate on cellular immunity," Comptes Rendus Acad. Sci., Ser. D., vol. 276(21),pp. 2915–2918, 1973.*
R. Ankenbauer et al., "Effects of Siderophores on the Growth of *Pseudomonas aeruginosa* in Human Serum and Transferrin", *Infect. Imm.*, 49 132–140 (1985).

V. Balasubramanian et al., "Growth Characteristics of Recent Sputum Isolates of *Mycobacterium tuberculosis* in Guinea Pigs Infected by the Respiratory Route", *Infect. Imm.*, 60 4762–4767 (1992).

V. Balasubramanian et al., "Mycobacterial Infection in Guinea Pigs", *Immunobiol.*, 191 395–401 (1994).

T.F. Byrd et al., "Interferon Gamma–activated Human Monocytes Downregulate Transferrin Receptors and Inhibit the Intracellular Multiplication of *Legionella pneumophila* by Limiting the Availability of Iron", *J. Clin. Invest.*, 83 1457–1465 (1989).

T.F. Byrd et al., "Regulation of Transferrin Receptor Expression and Ferritin Content in Human Mononuclear Phagocytes", *J. Clin. Invest.*, 91 969–976 (1993).

S.J. Cavalieri et al., "Synergistic Activities of Clarithromycin and Antituberculous Drugs against Multidrug–Resistant *Mycobacterium tuberculosis*", *Antimicrobial Agents and Chemotherapy*, 39 1542–1545 (1995).

V. Challu et al., "Recovery of Tubercle Bacilli From Urine of Pulmonary Tuberculosis Patients and its Comparison with the Corresponding Sputum Isolates", *Ind. J. Tub.*, 36 107–111 (1989).

C.R. Chitambar et al., "Inhibition of Leukemic HL60 Cell Growth by Transferrin–Gallium: Effects on Ribonucleotide Reductase and Demonstration of Drug Synergy With Hydroxyurea", *Blood*, 72 1930–1936 (1988).

C.R. Chitambar et al., "Regulatory Effects of Gallium on Transferrin–Independent Iron Uptake by Human Leukemic HL60 Cells", *Blood*, 80 505–511 (1992).

C.R. Chitambar et al., "Effects of Different Transferrin Forms on Transferrin Receptor Expression, Iron Uptake, and Cellular Proliferation of Human Leukemic HL60 Cells", *J. Clin. Invest.*, 78 1538–1546 (1986).

C.R. Chitambar et al., "Uptake of Gallium–67 by Human Leukemic Cells: Demonstration of Transferrin Receptor–dependent and Transferrin–independent Mechanisms", *Cancer Research*, 47 3929–3934 (1987).

P.H. Collery et al., "Dose Optimization of Gallium Chloride, Orally Administered, in Combination with Platinum Compounds", *Anticancer Research*, 14 2299–2306 (1994).

C.D. Cox, "Role of Pyocyanin in the Acquisition of Iron from Transferrin", *Infect. Immun.*, 52 263–270 (1986).

G.S. Douvas et al., "Gamma Interferon Activates Human Macrophages to Become Tumorcidal and Leishmanicidal but Enhances Replication of Macrophage–Associated Mycobacteria", *Infect. Immun.*, 50 1–8 (1985).

(List continued on next page.)

Primary Examiner—John Pak
(74) Attorney, Agent, or Firm—Mueting, Raasch & Gebhardt, P.A.

(57) ABSTRACT

This invention relates to the use of gallium-containing compounds, to inhibit intracellular pathogens including pathogens that are members of the genus Mycobacteria, Legionella, Histoplasma, and Leishmania and to organisms causing chronic pulmonary infection such *P. aeruginosa*.

18 Claims, 12 Drawing Sheets

OTHER PUBLICATIONS

G.S. Douvas et al., "Hypertriglyceridemic Serum, Very Low Density Lipoprotein, and Iron Enhance *Mycobacterium avium* Replication in Human Macrophages", *J. Infect. Dis.,* 170 1248–1255 (1994).

R.B. Fick, Jr., "Pathogenesis of the Pseudomonas Lung Lesion in Cystic Fibrosis", *Chest,* 96 158–164 (1989).

R.A. Finkelstein, et al., "Role of Iron in Microbe–Host Interactions", *Rev. Infect. Dis.,* 5, Suppl. 4, S759–S777 (1983).

B. Foster et al., "Gallium Nitrate: The Second Metal With Clinical Activity", *Cancer Treatment Rep.,* 70 1311–1319 (1986).

S.K. Furney et al., "Activities of Rifabutin, Clarithromycin, and Ethambutol against Two Virulent Strains of *Mycobacterium avium* in a Mouse Model", *Antimicrobial Agents and Chemotherapy,* 39 786–789 (1995).

P. Gangadharam et al., "Therapy of *Mycobacterium aviam* Complex Infections in Beige Mice with Streptomycin Encapsulated in Sterically Stabilized Liposomes", *Antimicrobial Agents and Chemotherapy,* 39 725–730 (1995).

P. Gangadharam et al., "Contributions of animal and macrophage models to the understanding of host parasite interaction of *Mycobacterium avium* complex (MAC) disease", *Res. Microbiol.,* 145 214–224 (1994).

C.D. Gaynor et al., "Pulmonary Surfactant Protein A Mediates Enhanced Phagocytosis of *Mycobacterium tuberculosis* by a Direct Interaction with Human Macrophages", *J. Immunology,* 5343–5351 (1995).

J. Gobin et al., "Exochelins of *Mycobacterium tuberculosis* Remove Iron from Human Iron–binding Proteins and Donate Iron to Mycobactins in the *M. tuberculosis* Cell Wall", *J. Exp. Med.,* 183 1527–1532 (1996).

T. Hartford et al., "Utilization of transferrin–bound iron by *Listeria monocytogenes*", *FEMS Microbiology Lett.,* 108 311–318 (1993).

C. Hershko, "Control of disease by selective iron depletion: a novel therapeutic strategy utilizing iron chelators", *Baillieres Clin. Haematol,* 7 965–1000 [Abstract No. 95186870] (1994).

M. Hickey et al., "Luciferase In Vivo Expression Technology: Use of Recombinant Mycobacterial Reporter Strains To Evaluate Antimycobacterial Activity in Mice", *Antimicrobial Agents and Chemotherapy,* 40 400–407 (1996).

N. Høiby, "Antibiotic Therapy for Chronic Infection of Pseudomonas in the Lung", *Annu. Rev. Med.,* 44 1–10 (1993).

P. Hopewell et al., "Evaluation of New Anti–Infective Drugs for the Treatment and Prevention of Tuberculosis", *Clin. Infect. Dis.,* 15(1) S282–S295 (1992).

J. Hubbard et al., "Effects of iron–limitation of *Escherichia coli* on growth, the respiratory chains and gallium uptake", *Arch. Microbiol.,* 146 80–86 (1986).

B. James et al., "Influence of Iron–Limited Continuous Cuture on Physiology and Virulence of *Legionella pneumophila*", *Infect. Immun.,* 63 4224–4230 (1995).

A.R. Jonkhoff et al., "Gallium–67 radiotoxicity in human U937 lymphoma cells", *Br. J. Cancer,* 67 693–700 (1993).

S.P. Klemens et al., "Activity of KRM–1648, a New Benzoxazinorifamycin, against *Mycobacterium tuberculosis* in a Murine Model", *Antimicrobial Agents and Chemotherapy,* 38 2245–2248 (1994).

B. Leyland–Jones, "Pharmacokinetics and Therapeutic Index of Gallium Nitrate", *Sem. Oncology,* 18 16–20 (1991).

J. Mönkkönen et al., "Liposome–Mediated Delivery of Gallium to Macrophage–Like Cells In Vitro: Demonstration of a Transferrin–Independent Route for Intracellular Delivery of Metal Ions", *Pharm. Res.,* 10 1130–1135 (1993).

N. Mor et al., "Inhibitory and Bactericidal Activities of Levofloxacin against *Mycobacterium tuberculosis* In Vitro and in Human Macrophages", *Antimicrobial Agents and Chemotherapy,* 38 1161–1164 (1994).

N. Mor et al., "MICs and MBCs of Clarithromycin against *Mycobacterium avium* within Human Macrophages", *Antimicrobial Agents and Chemotherapy,* 37 111–114 (1993).

S. Newman et al., "Inhibition of Growth of *Histoplasma capsulatum* Yeast Cells in Human Macrophages by the Iron Chelator VUF 8514 and Comparison of VUF 8514 with Deferoxamine", *Antimicrobial Agents and Chemotherapy,* 39 1824–1829 (1995).

R. North et al., "Mycobacterial Virulence. Virulent Strains of *Mycobacteria tuberculosis* Have Faster In Vivo Doubling Times and Are Better Equipped to Resist Growth–inhibiting Functions of Macrophages in the Presence and Absence of Specific Immunity", *J. Exp. Med.,* 177 1723–1733 (1993).

O. Olakanmi et al., "Acquisition of Iron Bound to Low Molecular Weight Chelates by Human Monocyte–Derived Macrophages", *J. Immun.,* 2691–2703 (1994).

I.M. Orme et al., "Animal and Cell–Culture Models for the Study of Mycobacterial Infections and Treatment", *Eur. J. Clin. Microbiol. Infect. Dis.,* 13 994–999 (1994).

C. Orosz et al., "Prevention of Murine Cardiac Allograft Rejection with Gallium Nitrate", *Transplantation,* 61 783–791 (1996).

P. Pal et al., "Immunization with Extracellular Proteins of *Mycobacterium tuberculosis* Induces Cell–Mediated Immune Responses and Substantial Protective Immunity in a Guinea Pig Model of Pulmonary Tuberculosis", *Infect. Immun.,* 60 4781–4792 (1992).

C. Perronne et al., "Sparfloxacin, Ethambutol, and Cortisol Receptor Inhibitor RU–40555 Treatment for Disseminated *Mycobacterium avium* Complex Infection of Normal C57BL/6 Mice", *Antimicrobial Agents and Chemotherapy,* 36 2408–2412 (1992).

L. Schlesinger, "Macrophage Phagocytosis of Virulent but Not Attenuated Strains of *Mycobacterium tuberculosis* Is Mediated by Mannose Receptors in Addition to Complement Receptors", *J. Immun.,* 150 2920–2930 (1993).

L. Schlesinger, "Phagocytosis of *Mycobacterium tuberculosis* is Mediated by Human Monocyte Complement Receptors and Complement Component C3", *J. Immun.,* 144 2771–2780 (1990).

P. Todd et al., "Gallium Nitrate—A Review of its Pharmacological Properties and Therapeutic Potential in Cancer–Related Hypercalcaemia", *Drugs,* 42 261–273 (1991).

E. Weinberg, "The Iron–Withholding Defense System", *ASM News,* 59 559–562 (1993).

R. Weiner, "The Role of Transferrin and Other Receptors in the Mechanism of $^{67}$Ga Localization", *Nucl. Med. Biol.,* 17 141–149 (1990).

M. Wilson et al., "Acquisition of Iron from Transferrin and Lactoferrin by the Protozoan *Leishmania chagasi*", *Infect. Immun.,* 62 3262–3269 (1994).

Grant Abstract for National Institute of Health Project No. AI33004, entitled "Macrophage Complement Receptors in Tuberculosis," FY 1995.

Grant Abstract for National Institute of Health Project No. AI34954, entitled "Pseudomonas Products, Oxygen Radicals, and Lung Injury," FY 1995.

C. R. Chitambar et al., "Inhibition of Ribonucleotide Reductase by Gallium in Murine Leukemic L1210," *Cancer Res.,* 51:6199–6201 (1991).

D. M. Mosser et al., "The Third Component of Complement (C3) is Responsible for the Intracellular Survival of *Leishmania major,*" *Nature,* 327: 329–331 (1987).

K. Raymond, NIH Grant Abstract entitled "Coordination Chemistry of Microbial Iron Transport," for Fiscal Year 1995.

M. E. Wilson et al., "The Major *Leishmania donovani chagasi* Surface Glycoprotein in Tunicamycin–Resistant Promastigotes," *J. Immunol.,* 144: 4825–4834 (1990).

S. D. Wright, "Receptors for Complement and the Biology of Phagocytes," *Inflamation: Basic Principles and Clinical Correlates,* Second Edition, p. 477, Edited by J.I. Gallin et al., Raven Press, Ltd., New York (1992).

Y. Yamamoto et al., "*Legionella pneumophila* Intracellular Growth in Normal vs. Immune Guinea Pig Macrophage Cultures," *Current Microbiogy,* 16: 333–336 (1988).

Y. Yamamoto et al., "Differential Morphologic and Metabolic Alterations in Permissive versus Nonpermissive Murine Macrophages Infected with *Legionella pnuemophila,*" *Infection and Immunity,* 60: 3231–3237 (1992).

G. Desai et al., "Killing of *Histoplasma capsulatum* by Macrophage Colongy Stimulating Factor–Treated Human Monocyte–Derived Macrophages: Role for Reactive Oxygen Intermediates," *J. Med. Microbiol.,* 43: 224–229 (1995).

S. E. McGowan et al., "Mechanisms of Serum–Enhanced Adhesion of Human Alveolar Macrophages to Epithelial Cells," *Lung,* 169: 215–226 (1991).

S. E. McGowan et al., "The Fate of Neutrophil Elastase Incorporated by Human Alveolar Macrophages," *Am. Rev. Respir. Dis.,* 127: 449–455 (1983).

N. Mor et al., "Comparison of Activities of Rifapentine and Rifampin Against *Mycobacterium tuberculosis* Residing in Human Macrophages", *Antimicrobial Agents and Chemotherapy,* 39: 2073–2077 (1975).

K. Abu–Dari et al., "Antimicrobial Activity of Thiohydroxamic Acids and their Metal Complexes: II. The Synthesis and Antimicrobial Activity of N–Methylthioacetohydroxamic Acid and its Zn, Cu, Fe and Ga Complexes", *Pur and Applied Sciences,* 20B, pp. 7–15 (1993).

National Asthma Education and Prevention Program, Expert Panel Report 2: Guidelines for the Diagnosis and Management of Asthma, Bethesda, Maryland, National Institutes of Health, NIH Publication No. 97–4051, pp. 1–146, (1997).

Gallin, (Chapter 26, Inflammation, In: Fundamental Immunology, $2^{nd}$ Ed., Paul (ed.) Raven Press Ltd., New York, pp. 721–733 (1989).

Olakanmi, O. et al., "Gallium inhibits growth of pathogenic mycobacteria in human macrophages . . . " Journal of Investigative Medicine, vol. 45, No. 3, p. 234A, Mar. 1997.*

* cited by examiner

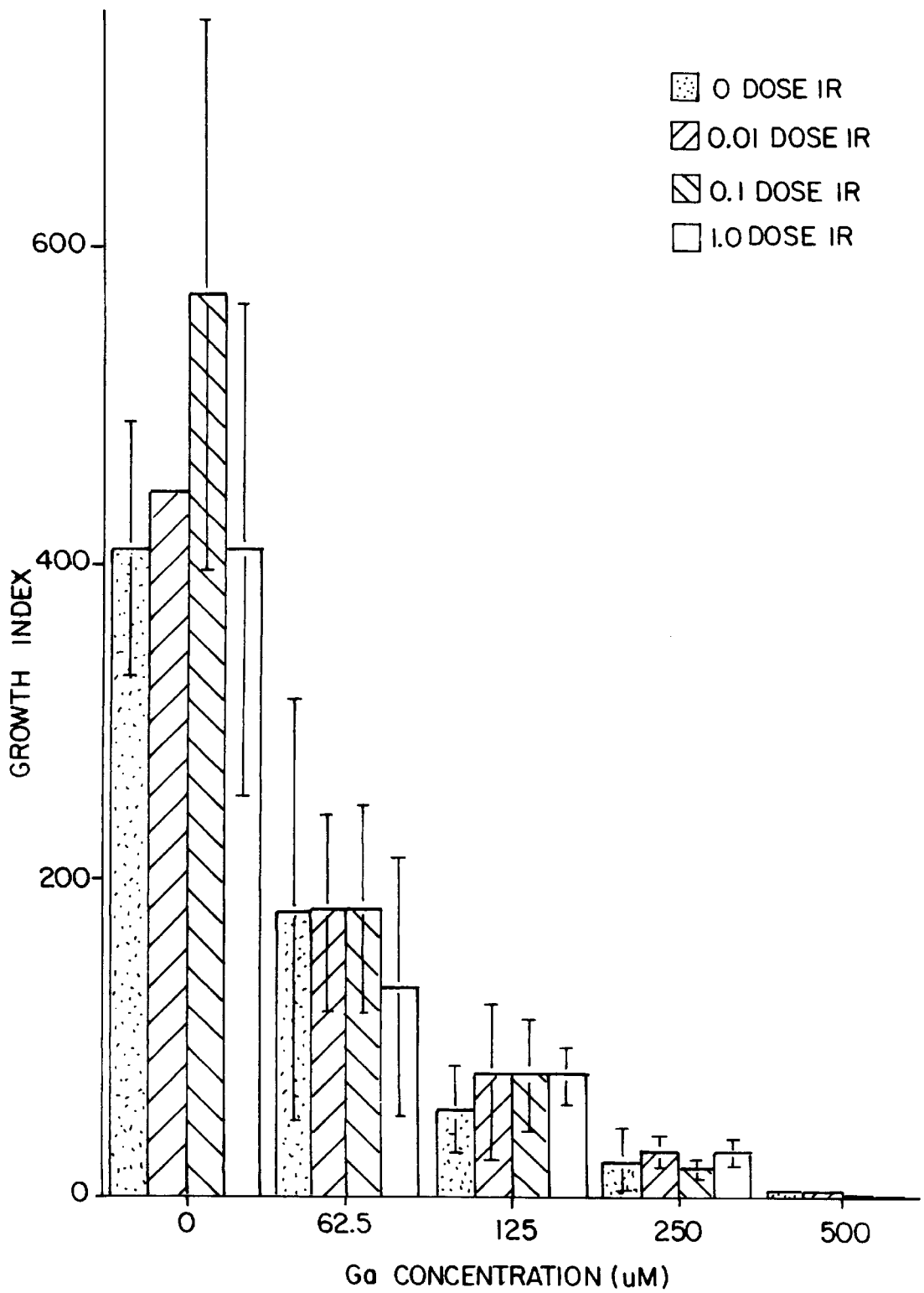

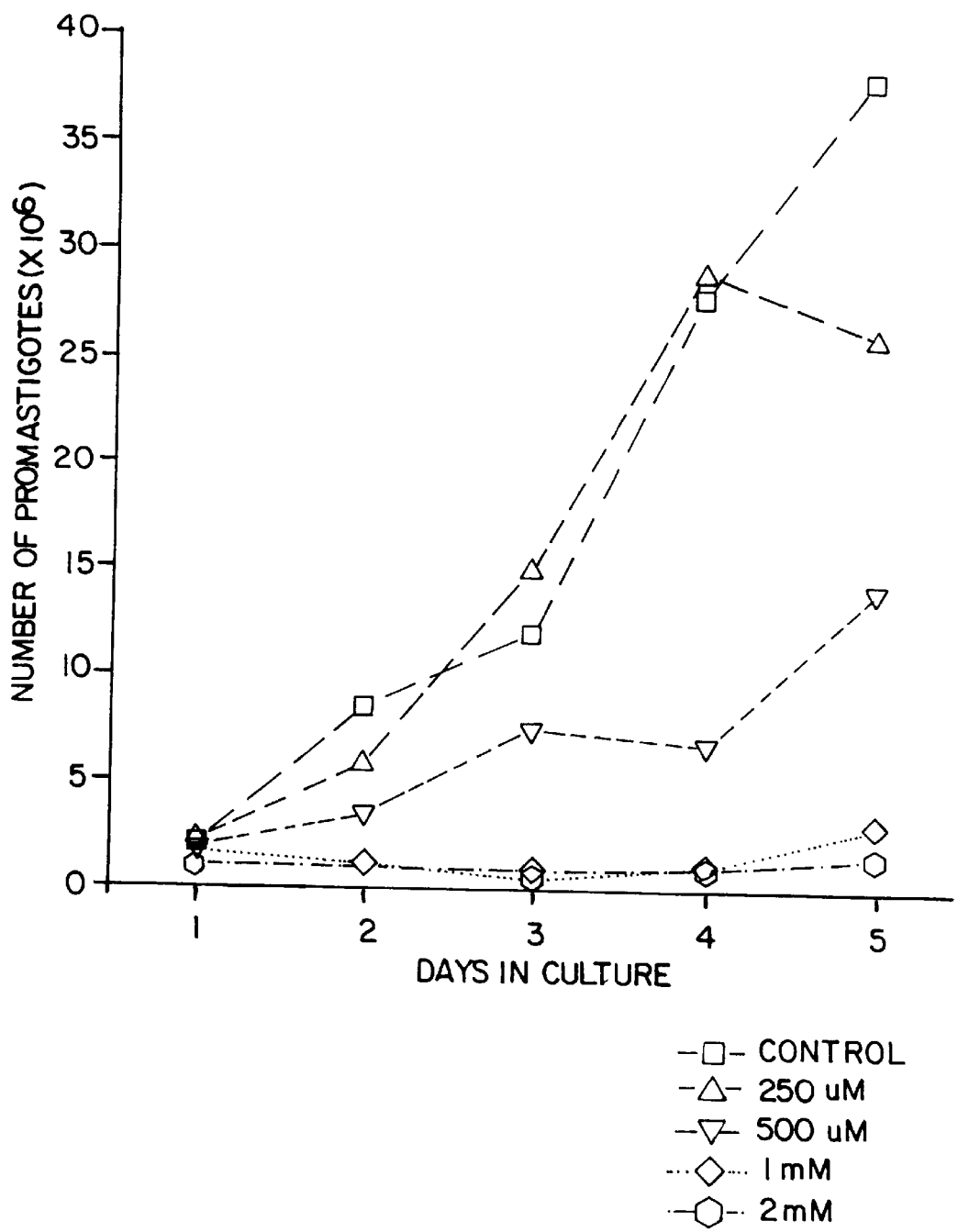

GALLIUM-CONTAINING COMPOUNDS FOR THE TREATMENT OF INFECTIONS CAUSED BY INTRACELLULAR PATHOGENS AND PATHOGENS CAUSING CHRONIC PULMONARY INFECTION

FIELD OF THE INVENTION

This invention relates to the treatment of infections caused by intracellular pathogens, such as M. tuberculosis and others and to pathogens that cause chronic pulmonary infections. In particular, this invention relates to methods for inhibiting the growth of intracellular pathogens and pathogens causing chronic pulmonary infections using gallium-containing compounds, and to methods to test the capacity of these compounds to inhibit growth of these pathogens in mononuclear phagocytes.

BACKGROUND OF THE INVENTION

This invention was made with government support under agreement numbers AI33004 and AI34954 awarded by the National Institutes of Health. The government has certain rights to this invention.

Intracellular pathogens include, but are not limited to, Mycobacteria species including M. tuberculosis, M. avium-intracellulare (MAI), and other intracellular pathogens including *Legionella pneumophila, Histoplasma capsulatum,* Leishmania species including *L. chagasi, L. donovani* and *L. major,* and the like. These organisms are characterized by their ability to be phagocytosed and sequestered in macrophages in patients infected with these organisms. In general, intracellular sequestration makes these organisms more difficult to treat with standard anti-bacterial therapies.

Tuberculosis is caused principally by the pathogenic agent *Mycobacterium tuberculosis* (M. tuberculosis) and more rarely by M. bovis or M. africanum. M. tuberculosis is an exemplary intracellular pathogen in that it, like other intracellular pathogens is phagocytosed in vivo by mononuclear phagocytes and becomes sequestered and/or grows within the phagocytic cell. Tuberculosis continues to be a major cause of worldwide morbidity and mortality, especially in the elderly and in immunocompromised patients, such as HIV (human immunodeficiency virus)-infected persons. The World Health Organization estimates that 1.7 billion persons, or one third of the world's population, are infected with tuberculosis. New estimates indicate that there are approximately 10 million new cases of tuberculosis annually with three million deaths associated with tuberculosis worldwide.

The only current vaccine for M. tuberculosis is the BCG vaccine. This vaccine is a live attenuated strain of *Mycobacterium bovis.* The vaccine produces variable results and may rarely initiate active tuberculosis infection in compromised vaccinees. A significant problem associated with the vaccine is that it results in the conversion of the tuberculin skin test (PPD) from negative to positive. The tuberculin skin test is still the primary test of choice for diagnosing exposure to M. tuberculosis. Therefore, individuals receiving the BCG vaccine test positive using the tuberculin skin test making patient monitoring for M. tuberculosis exposure more difficult. Until such time that a uniformly effective vaccine exists, novel therapeutic approaches that significantly reduce the duration of therapy will have a major impact on compliance and ultimately on the transmission of this disease.

Current therapies to treat tuberculosis are becoming less satisfactory because of a growing incidence of drug-resistant strains of M. tuberculosis. Effective therapy for active tuberculosis requires multiple types of antibiotics taken for a minimum of six months. Each of these antibiotics causes sizable morbidity from drug toxicity. Further, poor compliance, in part due to the duration of treatment and side effects of the antibiotics, remains a critical issue in the treatment of tuberculosis. Improper treatment of M. tuberculosis infection has led directly to a growing incidence of multi-drug resistant tuberculosis leading to prolonged infectiousness and thereby enhanced transmission potential.

MAI is the most common mycobacterial pathogen in AIDs patients. Up to 50% of this population will develop infection due to MAI in their lifetime. MAI are inherently multi-drug resistant and treatment for these patients currently requires taking multiple types of antibiotics for life. Infections due to the other intracellular pathogens described above are also more commonly seen in the growing population of immunocompromised patients with significant morbidity and in some cases mortality. In these cases patients are also treated with multiple antimicrobial agents for a significant length of time.

The problems associated with Mycobacterium infection are also true for diseases associated with other intracellular pathogens. There is currently a need for new methods to treat intracellular pathogens such as M. tuberculosis.

Patients with cystic fibrosis are at risk for a variety of pulmonary infections, including those due to mycobacterial pathogens and also including *Pseudomonas aeruginosa,* (*P. aeruginosa*) an extracellular pathogen that chronically inhabits the airways of the lungs in these patients requiring long term antibiotic therapy. Pseudomonas aeruginosa causes significant morbidity and mortality in cystic fibrosis patients (see Fick, R. B., Jr. Chest 96:158–164, 1989 and Hoiby, N. Annu. Rev. Med. 44:1–10, 1993).

SUMMARY OF THE INVENTION

This invention relates to methods for treating intracellular pathogens infecting mononuclear phagocytes using gallium-containing compounds, including gallium nitrate. In a preferred embodiment of this invention, a method is disclosed for inhibiting growth of an intracellular pathogen comprising the step of delivering a therapeutically effective dose of a gallium-containing compound in a pharmaceutically acceptable buffer to a mammalian cell. In one embodiment the pathogen is inside a mammalian cell. In a preferred aspect of this embodiment, the method also includes the step of treating the cell with at least a second compound known to inhibit the growth of the intracellular pathogen. The second compound can be an antibiotic or another compound and where the second compound is an antibiotic, the antibiotic is preferably selected from the group consisting of streptomycin, isoniazid, rifampin, pyrazinamide and ethambutol.

In another preferred aspect of this embodiment, the pathogen is a member of the genus Mycobacterium and the pathogen can be a multi-drug resistant strain of the genus Mycobacterium. In yet another preferred aspect of this embodiment, the pathogen is selected from the group consisting of Legionella, Histoplasma and Leishmania.

The therapeutic ranges for the gallium-containing compounds include concentrations ranging from 16.25 $\mu$M to greater than 1000 $\mu$M. The literature indicates that safe doses of gallium nitrate for cancer patient therapy extends in one set of studies up to at least about 200 mg/m$^2$/day. This invention employs therapeutically effective doses of at least 50 mg/m$^2$/day and greater and limited only by toxicity studies in patient testing (see for example, Foster, et al. *Cancer Treatment Reports* 70:1311–1319, 1986).

In another aspect of this invention the delivering step comprises delivering the therapeutically effective dose to a patient infected with the intracellular pathogen or delivering the therapeutic effective dose in vitro and preferably delivering the therapeutic effective dose to a cell in vitro. The therapeutically effective dose is preferably delivered intravenously, subcutaneously, by aerosol or orally. The therapeutically effective dose may be delivered using liposomes and in this application, the liposomes are preferably combined with the gallium-containing compound before the delivering step. The method can also additionally comprise the step of delivering interferon-γ to the cell.

In another embodiment of this invention, the invention relates to a composition for inhibiting the growth of an intracellular bacterial pathogen where the composition comprises a gallium-containing compound and an antibiotic known to inhibit growth of the intracellular bacterial pathogen. In a preferred aspect of this embodiment, the gallium-containing compound is gallium nitrate and the antibiotic is preferably selected from the group consisting of streptomycin, isoniazid, rifampin, pyrazinamide and ethambutol. In another embodiment of this invention, the invention relates to a composition for inhibiting the growth of an intracellular pathogen where the composition comprises a gallium-containing compound and interferon-γ.

In yet another embodiment of this invention, the invention relates to a method for determining the sensitivity of an intracellular pathogen to a gallium-containing compound where the method comprises the steps of: treating a mononuclear phagocyte infected with an intracellular pathogen with at least one concentration of the gallium-containing compound; and determining if the growth of the intracellular pathogen is inhibited by the gallium-containing compound. The mononuclear phagocyte is preferably a human monocyte, a macrophage or a human alveolar macrophage. The intracellular pathogen is preferably a Mycobacterium, including drug-resistant strains of Mycobacterium and in a preferred embodiment, the gallium-containing compound is gallium nitrate.

In one aspect of this method, the treating step preferably further comprises treating the phagocyte with a second compound known to inhibit the growth of the intracellular pathogen and/or treating the phagocyte with interferon-γ.

In yet another embodiment of this invention, a method is disclosed for inhibiting *P. aeruginosa* growth, where the method comprises the step of contacting *P. aeruginosa* with a therapeutically effective dose of a gallium-containing compound in a pharmaceutically acceptable buffer. In one aspect of this method, the method further comprises the step of administering the therapeutically effective dose of the gallium-containing compound to the lung of a patient. The therapeutically effective dose of the gallium-containing compound is administered intravenously, orally, or administered directly to the lungs, such as by aerosol.

BRIEF DESCRIPTION OF THE DRAWINGS

FIG. 1 provides histograms that illustrate the inhibitory effect of gallium nitrate on *M. tuberculosis* in broth culture.

FIG. 7 illustrates the results of experiments demonstrating the effectiveness of gallium-containing compounds as compared to combination Isoniazid, Rifampin (IR) drug therapy on the inhibition of growth of a multi-drug resistant strain of *M. tuberculosis*.

FIG. 9 illustrates the results of experiments demonstrating the ability of gallium nitrate to inhibit *Leishmania chagasi*.

DETAILED DESCRIPTION OF THE INVENTION

Figure 1A:
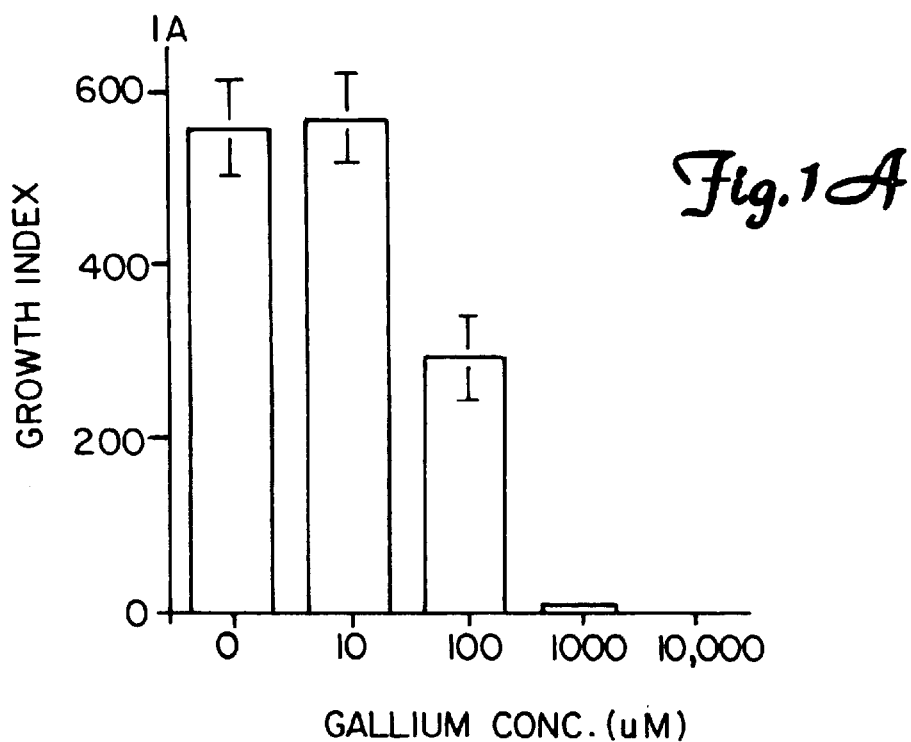
FIG. 1A demonstrates the inhibitory effect of gallium nitrate on the attenuated *M. tuberculosis* strain H37Ra in broth culture over 0 to 10,000 μM concentrations of gallium nitrate.
Figure 1B:
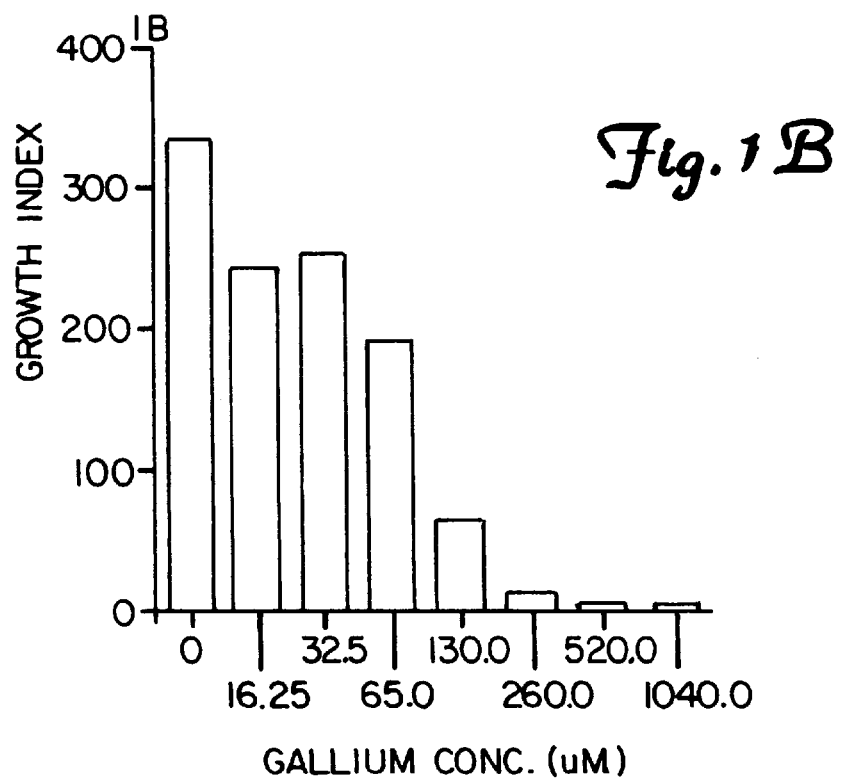
FIG. 1B illustrates the results of experiments to inhibit *M. tuberculosis* strain H37Ra in broth culture over the range of 0 to 1040 μM concentrations gallium nitrate.
Figure 2A:
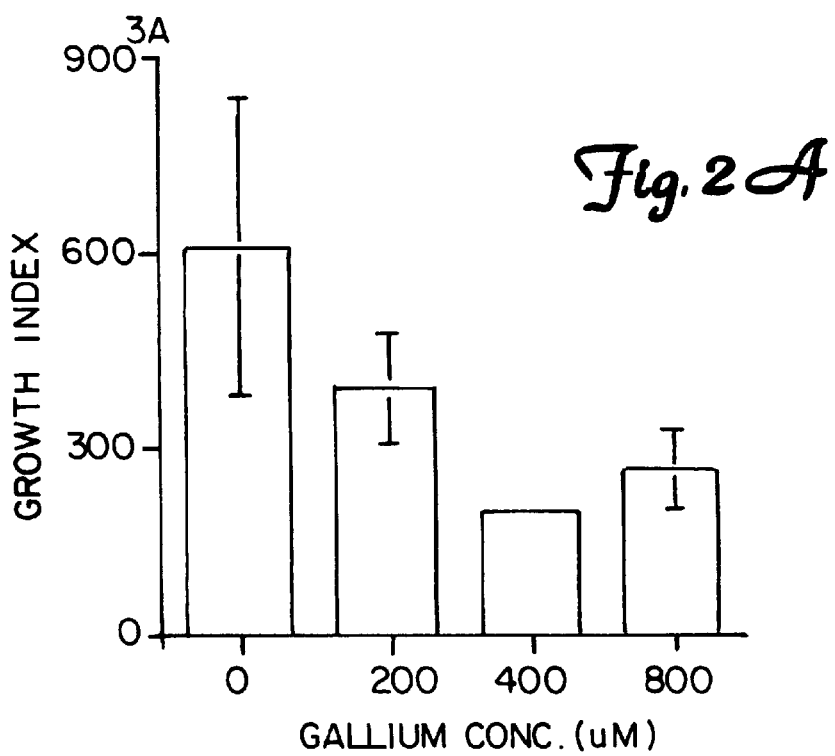
FIG. 2 illustrates results demonstrating the ability of gallium nitrate to inhibit the growth of two strains of *M. tuberculosis* in human macrophages. Monocyte derived macrophages (MDM) containing strain H37Ra were incubated for 24 h (FIG. 2A), 48 h (FIG. 2B) or 72 h (FIG. 2C) and macrophages containing the virulent strain Erdman were incubated for 24 h (FIG. 2D) or 48 h (FIG. 2E) in gallium nitrate.
Figure 2B:
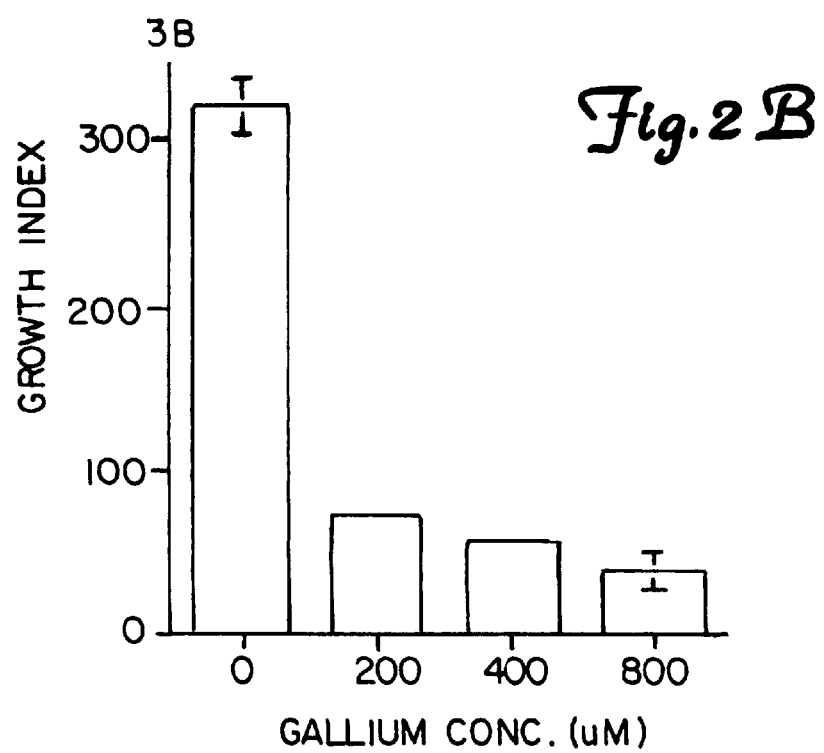
Figure 2C:
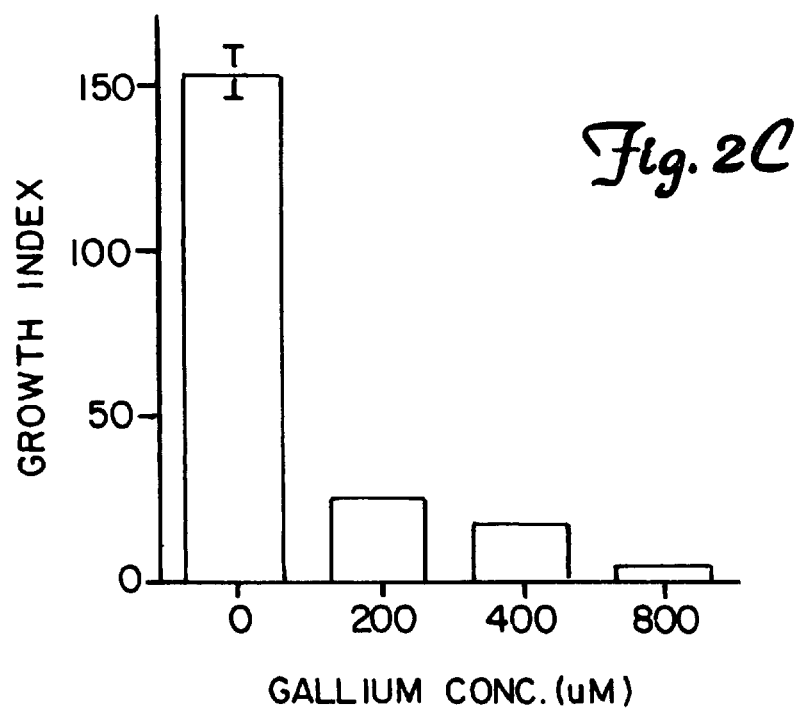
Figure 2D:
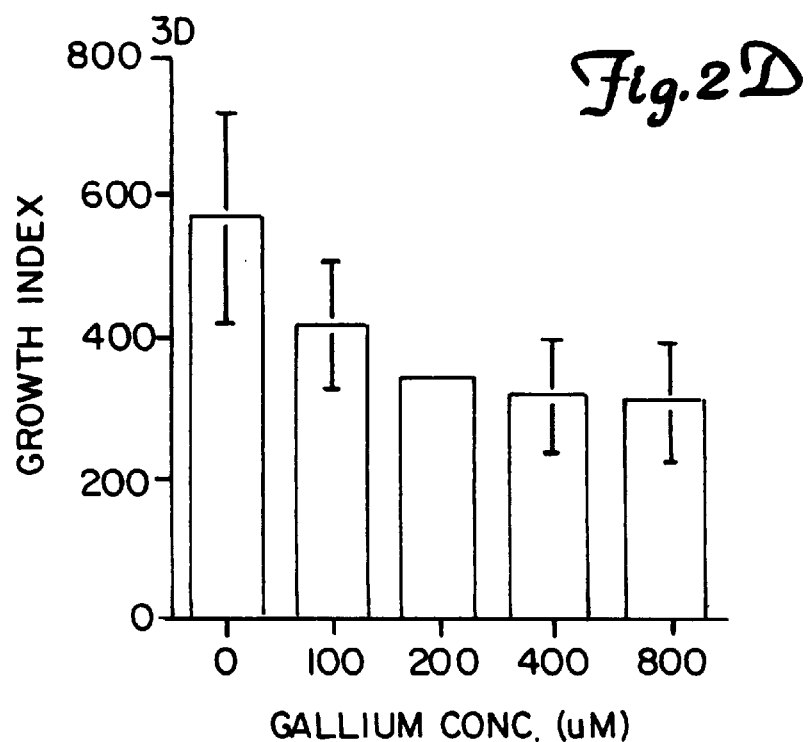
Figure 2E:
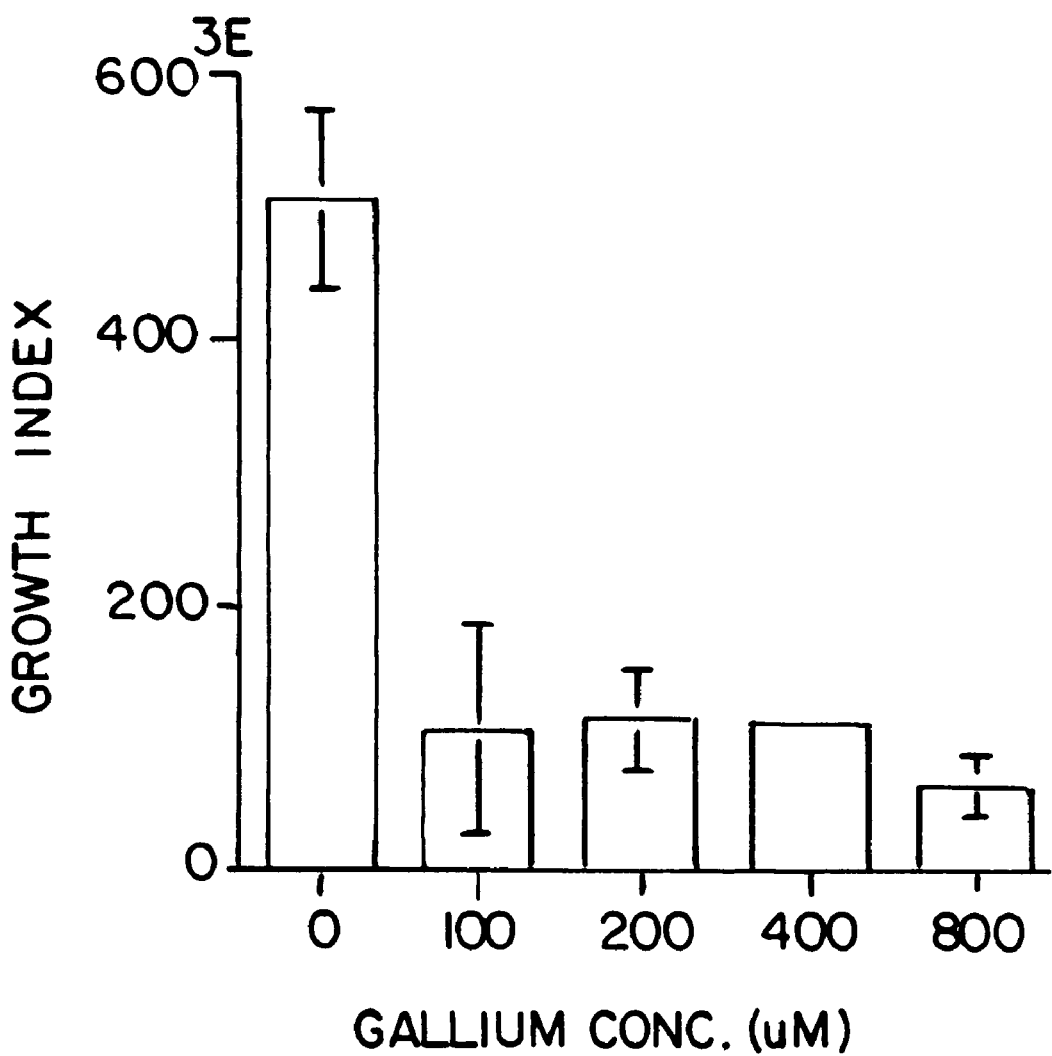

*M. tuberculosis* is one of a group of human pathogens that enters, multiplies, and can be sequestered within mononuclear phagocytes. These pathogens rely on previously acquired iron or on the acquisition of iron from intracellular stores of the host cell to meet their metabolic needs.

Pathogens such as *M. tuberculosis* have developed high affinity iron-binding molecules, termed siderophores, to obtain iron in environments where iron stores are limited. These molecules can scavenge iron from intracellular host-binding molecules. *M. tuberculosis* produce at least two iron-binding molecules. The first, termed exochelins, bind iron in the extracellular aqueous environment. A second type, mycobactin, is a high affinity lipophilic iron-binding molecule located in the cell wall of *M. tuberculosis*. *P. aeruginosa* has two well characterized siderophores; pyoverdin and pyochelin (Aukenbauer, R. et al. *Infect. Immun.* 49:132–140, 1985).

Gallium is a group IIIa transition metal that has been used in nuclear medicine as a means for localizing neoplasms and inflammatory sites. Gallium localizes to these sites because of the predilection of gallium for certain neoplastic and inflammatory cells. Gallium has also been used therapeutically for malignant neoplasms and malignancy-associated hypercalcemia (For example, see Foster, et al. *Cancer Treat Rep* 70:1311–1319, 1986; Todd, et al. *Drugs* 42:261–273, 1991; and, Jonkoff et al. *Br. J. Cancer* 67:693–700, 1993). It is also known that gallium can accumulate in cells of mononuclear origin in the liver, kidney, spleen and lymphatic system. Clinical experience in patients with cancer-related hypercalcemia indicates that gallium nitrate is well tolerated, producing few clinically relevant adverse effects (see Todd, et al., supra and Leyland-Jones, *Semin Oncol* 18:16, 1991).

Without intending to limit the scope of this invention, the effects of gallium appear to be related to its ability to substitute in many biomolecular processes for $Fe^{3+}$ (For example see Chitambar, et al. *Cancer Res.* 51:6199–6201, 1991; Chitambar, et al. *Blood* 72: 1930, 1988; and, Chitambar, et al. *J. Clin Invest* 78:1538–1546, 1986). For example, $Ga^{3+}$ functions like $Fe^{3+}$ in that both bind to transferrin and are transported into cells via transferrin receptor-mediated endocytosis (Chitambar, et al. *Cancer Res.* 47:3929–3934, 1987). Gallium and iron are both taken up into the cell and incorporated into the iron storage protein, ferritin (see Chitambar, *Cancer Res.*, supra). It has also been observed that gallium and iron can be taken up by the myeloid tumor cell lines, U937 and HL60, via a transferrin-independent mechanism.

This invention relates to the use of gallium-containing compounds, such as for example, gallium nitrate, to inhibit the growth of intracellular pathogens in mononuclear phagocytes (monocytes and macrophages). While the preferred compound for treating intracellular pathogens is gallium nitrate; gallium chloride, gallium conjugates including gallium transferrin and other gallium-containing compounds are also contemplated in this invention. The term "inhibiting growth" is used herein to refer to situations in which there is no multiplication of the organism in question. No organism multiplication includes both organism stasis and organism death.

The compounds of this invention are useful for treating a variety of infections caused by intracellular pathogens including, but not limited to, Mycobacterium species including *M. tuberculosis, M. africanum, M. bovis,* MAI, and other intracellular pathogens including *Legionella pneumophila*, Leishmania species including *L. chagasi, L. donovani* and *L. major, Histoplasma capsulatum,* and the like. These compounds are also potentially useful for the treatment of infections caused by pathogens such as *P. aeruginosa* that cause chronic pulmonary infections in cystic fibrosis patients.

In one embodiment, the invention relates to a method for inhibiting the growth of intracellular pathogens and *P. aeruginosa* using gallium-containing compounds. In one aspect of this embodiment, an assay is disclosed to detect the ability of gallium nitrate or gallium transferrin to inhibit *M. tuberculosis*. In addition to *M. tuberculosis,* these assays are useful to permit those skilled in the art to assess the sensitivity of various types of pathogens to inhibition or killing by gallium-containing compounds or combinations of compounds. Combinations of compounds contemplated in this invention include, for example, at least one gallium-containing compound and a second chemical or compound, such as an antibiotic known to inhibit the pathogen (i.e. for example, in the case of *M. tuberculosis,* antibiotics including, but not limited to, streptomycin, isoniazid, rifampin, fluoroquinolones, sparfloxacin, and/or ethambutol) or agents known to down-regulate iron uptake, including, but not limited to, IFN-γ, and the like.

In vitro cell cultures are accepted by those skilled in the art as assays for determining the susceptibility of *M. tuberculosis* and other intracellular pathogens to inhibitory compounds. For example, Mor, et al. indicate that they have employed in vitro assays to determine the susceptibility of *M. tuberculosis* to agents that inhibit growth of these organisms in macrophages in anticipation of controlled clinical trials Mor et al. (*Antimicrobial Agents and Chemotherapy* 39:2073–2077, 1975). A variety of assays are known to mimic physiological conditions and these include, but are not limited to Mor, et al. (supra) and Mor et al., *Antimicrobial Agents and Chemotherapy* 38:1161–1164, 1994.

In the assays, cells susceptible to infection by *M. tuberculosis*, MAI or other intracellular pathogens are placed in culture in vitro. There are a number of different cell types that can be used in this invention that are susceptible to intracellular pathogens. In particular, the assays of this invention employ mononuclear phagocytes. These cells include macrophages and circulating monocytes. Mononuclear phagocytes can be obtained as established cells lines or as primary cells taken from a patient, where the patient cells are placed into culture and used within several months. Primary human monocytes, tissue monocyte-derived macrophages (MDMs) or myeloid cell lines including HL60, U937 or THP-1 cells can be used. Myeloid cell lines are known in the art and are readily available from the ATCC (American Type Culture Collection, Rockville Md.). Human macrophages are preferred for assessing the susceptibility of a particular strain of Mycobacterium, or another intracellular bacterial pathogen, to gallium-containing compounds where the data will be used for human applications. Primary phagocytes are particularly preferred and primary alveolar macrophages are most preferred to assess the sensitivity of a particular gallium-containing compound to intracellular pathogens, such as *M. tuberculosis* that infect the airways of the lung.

Peripheral blood mononuclear cells (PBMC) can be used to generate primary monocytes and MDMs. These cells are readily isolated from heparinized blood on Ficoll-sodium diatrizoate gradients (Pharmacia Fine Chemical, Piscataway, N.J.) or the like. PBMC are cultured on TEFLON® wells (Savillex Corp., Minnetonka, Minn.) at about 1.5 to about $2.0 \times 10^6$ mononuclear cells/ml and the monocytes or MDMs subsequently purified by adherence to glass or plastic.

Isolated alveolar macrophages can be obtained using lung lavage collection methods well known in the art. For lavage methods and the isolation of alveolar macrophages from the bronchial lavage fluid see McGowan, et al. *Lung* 169:215–226, 1991 and McGowan, et al. *Am. Rev. Respir. Dis.* 127:449–455, 1983 respectively.

A variety of microbial pathogens, including the commercially available microbial strains used in the examples below, are available from the ATCC (American Type Culture Collection, Rockville, Md.) including strains of *M. tuberculosis, M. africanum, M. bovis,* MAI, and other intracellular pathogens including *Legionella pneumophila,* Leishmania species including *L. chagasi, L. donovani* and *L. major,* as well as *Histoplasma capsulatum,* and the like. *M. tuberculosis* strains including H37Ra, H37Rv and the Erdman strain (all available from the ATCC) are preferred test strains because these strains are well characterized. Those skilled in the art will recognize that a variety of other *M. tuberculosis* strains including patient isolates are also useful to test the inhibitory capacity of gallium-containing compounds.

Suspensions of bacterial pathogen can be tested in broth culture initially, if necessary or desired, to determine whether or not the gallium-containing compound or compounds directly inhibit the growth of the pathogen in suspension culture. Example 1 details methods for performing the growth index assays of this invention to detect the growth of pathogenic organisms including *M. tuberculosis* in suspension culture. There are a number of suspension culture methods known in the art. As an example of a suspension assay, *M. tuberculosis* growth and gallium nitrate inhibition were quantitated using the radiometric BACTEC 460TB system (Becton Dickinson Diagnostic Instrument Systems, Sparks, Md.). The results from these experiments demonstrated that gallium nitrate was effective at inhibiting the growth of *M. tuberculosis* in a dose-dependent fashion with statistically significant inhibition observed at 16.25 $\mu$M gallium nitrate and marked inhibition at approximately 100 $\mu$M gallium (see Example 1 and the results illustrated in FIG. 1). While this and other examples are directed to the inhibition of Mycobacteria, those skilled in the art will recognize that the assays are readily adaptable to the quantitation of other intracellular bacterial pathogens capable of infecting phagocytic cells. Growth inhibition of parasites or fungi can also be readily assessed by introducing the gallium-containing compounds into cultures of the organisms under standard growth conditions.

The gallium-containing compounds can also be tested for their ability to inhibit intracellular pathogens in tissue culture assays. In general, in these assays, the macrophages are placed in culture and incubated with the intracellular pathogen at an approximate cell to pathogen ratio of preferably at least 1:1 to about 1:5 cells:pathogen. Exemplary culture conditions are provided in the assays detailed in the Examples. For assays assessing *M. tuberculosis* infection, freshly adherent monocytes, 12 day-old adherent MDMs, or freshly adherent alveolar macrophages are incubated with *M. tuberculosis,* MAI or other intracellular bacteria at a ratio of about 1:1 to about 1:5 (phagocyte:bacterium). For *M. tuberculosis* or MAI, the bacteria are incubated with the phagocyte for 2 hr at 37° C. in RPMI/HEPES media with 2.5% serum or human serum albumin (serum-free). The cells are washed to remove non-adherent bacteria and monolayers are replated with RPMI containing 1% autologous serum (to maintain phagocyte viability but not to sustain extracellular growth of bacteria). Gallium-containing compounds, such as gallium nitrate, with, or without, other agents such as antibiotics, cytokines etc., are added about 24 hr. later and mycobacterial growth in cell lysates is then assessed over the next several days either by the radiometric BACTEC system or by colony-forming units on agarose plates. In each experiment, growth is assessed relative to control monolayers where no drug has been added.

To test the ability of gallium to inhibit growth of *M. tuberculosis* in cells, human monocyte derived macrophages (MDMs, Example 2 and FIG. 2) and human alveolar macrophages (HAMs, Example 3 and FIG. 3) were infected with *M. tuberculosis.* Comparing the results in the two cell types is important because virulent mycobacteria have the capacity to grow progressively in the lungs despite the presence of a functioning CD4 T-cell immunity that is able to control mycobacterial growth in other organs (North, et al. *J. Exp. Med.* 177:1723–1733, 1993). Macrophage assays to test various treatment regimes for *M. tuberculosis* therapy are accepted in the art as indicative of in vivo utility. For example, the importance of studying the effects of bacterial growth in broth media and the evaluation of mycobacteriocidal activity in *M. tuberculosis*-infected human macrophages has been emphasized by Hopewell, et al. (see *Clin Infect Dis* 15 Suppl 1:S282, 1992). To test the inhibitory effect of gallium nitrate on both virulent and attenuated strains of *M. tuberculosis,* macrophages were infected before receiving gallium nitrate. For each set of experiments macrophage monolayer integrity and viability were monitored. Results indicated that the gallium-containing compound, gallium nitrate, killed *M. tuberculosis* sequestered within human macrophages.

Example 4 and Example 5 detail exemplary methods used to determine whether the mycobacteria strains were killed by the addition of gallium nitrate. Here, media from test samples demonstrating no mycobacteria growth over time were removed and the mycobacteria were pelleted by centrifugation. The bacteria were resuspended in 7H9 broth (BBL Microbiology Systems) or onto agar plates without gallium nitrate and incubated under conditions known to promote bacterial growth. In Example 4, the growth index for these cultures was assessed after 6 weeks to determine whether bacteria are inhibited or killed. The results indicated that the bacteria were killed. In Example 5, *M. tuberculosis*-infected macrophages cell lysates were plated onto the surface of media able to support *M. tuberculosis* growth. Colony forming unit assays were counted to assess bacterial death or inhibition. The results (see FIG. 5) indicated that *M. tuberculosis* were killed by gallium nitrate.

Those skilled in the art will recognize that there are other assays that could be used to assess growth inhibition including assays to differentiate between pathogen stasis or pathogen death by plating cell lysates onto or into media known to support growth of the particular pathogen. In addition, recombinant mycobacteria and reporter mycobacteriophages expressing firefly or bacterial luciferase to measure the susceptibility of *M. tuberculosis* to gallium can also be used. These assays employ mycobacterial reporter strains and measure changes in luciferase expression (see Hickey et al. *Antimicrob. Agents and Chemotherapy* 40:400–407, 1996).

In experiments to demonstrate the inhibition of intracellular pathogens such as *M. tuberculosis* by other gallium-containing compounds, gallium was complexed with transferrin and used in varying ratios to determine its effect on bacterial growth (See Example 6). These experiments are important to in vivo applications because when gallium nitrate is infused in vivo, most of the gallium binds rapidly to serum transferrin. Thus, these experiments more closely resemble physiologic conditions. FIG. 4 details the results of this study. Marked inhibition of growth in the presence of gallium transferrin was seen at a lower concentration of gallium than that observed when gallium nitrate was use as in FIG. 4. The results employing gallium transferrin support the conclusion that gallium is useful in vivo for inhibiting growth of *M. tuberculosis* and indicate that gallium transferrin, the major form that gallium nitrate will be converted to in the blood, is active against *M. tuberculosis.*

The cell toxicity of gallium-containing compounds for a particular cell type can be tested in vitro. Gallium nitrate was applied to infected and uninfected cells to assess gallium toxicity. Results of the studies assessing gallium nitrate toxicity in culture are provided in Examples 7 and 8. Results indicated that gallium nitrate is not toxic at 1 mM dosage levels in vitro. Gallium nitrate is also non-toxic in vivo at doses of at least 200 mg/m$^2$/day and at plasma concentrations greater than 1.2 mg/L. Gallium has been used in cancer patients in large scale clinical studies and did not affect bone cell morphology or viability despite the ability of gallium nitrate to accumulate in these cells (see Todd et al., *Drugs,* 42(2):261–273, 1991).

Since human patient studies have demonstrated that gallium nitrate is not toxic over a wide range of doses, it is anticipated that extensive animal studies will not be required. However, animal studies are useful for assessing the efficacy of gallium-containing compounds to inhibit intracellular pathogens in vivo. Example 9 details studies to assess efficacy in animal models. Initial studies can be conducted in small animals including mice and guinea pigs. Both mice and guinea pigs are art accepted models for studying the effect of antimicrobial agents active against intracellular pathogens including *M. tuberculosis* and MAI (see, for example, studies including Perronne, et al. *Antimicrobial Agents and Chemotherapy* 36:2408–2412, 1992 and Hickey, et al. *Antimicrobial Agents and Chemotherapy* 40:400–407, 1996, Balasubramanian et al. *Immunobiol.* 191:395–401, 1994 and the review by Gangadharam et al. *Res. Microbiol.* 145:214–224, 1994).

The guinea pig is an excellent animal model to study pulmonary tuberculosis (Pal et al. *Infection. and Immunity* 60:4781–4792, 1992) and guinea pigs are a known model for *L. pneumophila* disease. The guinea pig responds to *M. tuberculosis* like humans in that guinea pigs are susceptible to infection with low doses of aerosolized microbes. Like human infections, the lesions are characterized by Langhans giant cells and they exhibit a cutaneous delayed-type hypersensitivity reaction to PPD with induration characterized by a dense mononuclear cell infiltrate (Balasubramanian et al. *Inf and Inm.* 60:4762–4767, 1992).

Preferably animals are infected with an aerosolized dose of intracellular pathogen where the primary route of infection for the intracellular pathogen is through the airways. Alternatively, the animals can be infected with a dose of intracellular pathogen given intravenously or by another route. Both intravenous and aerosolized routes of infection for animal studies related to intracellular pathogens are known in the art (for example, see Hickey, et al. supra and Pal, et al. *Inf. and Imm.* 60:4781–4792, 1992). Once infected, or prior to infection, the animals are given various concentrations of a gallium-containing compound, such as gallium nitrate. Animals are sacrificed over time and lung tissue and other tissues are assessed for the extent of infection by the intracellular pathogen over time. In preclinical toxicological studies to determine the effect of gallium nitrate as a cancer treatment, gallium nitrate was administered to a variety of animals including mice, rats, rabbits, guinea pigs, dogs and monkeys (Foster et al. supra).

Once animal studies are completed, gallium-containing compounds are delivered to a patient infected with an intracellular pathogen. The gallium-containing compound, such as gallium nitrate, is delivered to patients in a variety of methods known in the art. The composition can be delivered intravenously, orally or nasally, subcutaneously, by aerosol and the like. Several methods of delivery have been tested in studies to determine the effect of gallium-containing compounds as antineoplastic agents. An example using intravenous administration of gallium nitrate is provided in Example 10. Gallium nitrate, or another gallium-containing compound, can be suspended in an acceptable pharmaceutical buffer such as phosphate buffered saline, or the like, for administration to the patient.

The term "pharmaceutically acceptable" refers to a material that is not biologically or otherwise undesirable. The material can be administered along with the gallium-containing compounds of this invention without causing undesirable biological effects nor does the pharmaceutically acceptable buffer interact in a deleterious manner with the gallium-containing compound, nor with any other component of the pharmaceutical composition in which it is contained. Those with skill in the art will recognize that a variety of suitable formulations can be readily prepared and delivered to a patient, particularly in view of the past experimentation with gallium-containing compounds related to their antineoplastic properties.

Based on the results of the use of gallium nitrate and gallium transferrin to inhibit *M. tuberculosis* in cells in culture and in view of the in vivo testing of gallium nitrate and other gallium-containing compounds in cancer patients, it is contemplated that continuous intravenous infusion of less than 900 $mg/m^2$ per day, preferably greater than at least about 50 $mg/m^2$/day, more preferably administered doses range between about 100 to about 750 $mg/m^2$/day and, still more preferably, about 100 to about 350 $mg/m^2$ per day or a steady-state plasma gallium concentration of about 0.2 to about 5 mg/liter and, preferably, about 1.0 to about 2.0 mg/liter can be achieved within 48 hr (Todd, et al. supra). Higher concentrations of intravenous infusion can also be safely administered for short periods of time. Pharmacokinetic studies were performed by Todd et al., (supra), by Leyland-Jones (*Semi. Oncol.,* 18(4) Suppl., 5:16–20 1991) and others related to the use of gallium-containing compounds in cancer patients.

Gallium chloride oral formulations have been used to treat inoperable non-small cell lung cancers. Dosages ranged from at least 100 mg/24h to 1400 mg/24 h without substantial toxic effect (Collery, et al. *Anticancer Research* 14:2299–2306, 1994). Oral doses, within the ranges of gallium chloride tested in human toxicological tests are used to treat the pathogens of this invention.

Gallium nitrate may also be combined and encapsulated into negatively charged liposomes to provide a transferrin-independent route for intracellular delivery of gallium into macrophages. Liposomes of gallium nitrate were prepared by Monkkonen, et al. (see *Pharm Res* 10:1 130–1135, 1993) for in vitro studies. Methods for delivering liposomes containing drug to a cell either in vitro or in vivo are known in the art. For example, liposomes have been used to deliver agents known to inhibit *M. tuberculosis* (see Gangadharam, et al. *Antimicrob. Agents and Chemotherapy* 39:725–730, 1995). Preferred liposomes for the delivery of agents to inhibit *M. tuberculosis* include PEG-DSPE-DSPC-chol, PI-DSPC-chol (both in preferred molar ratios of 1:9:6.7) and others. Gallium nitrate, or other gallium-containing compounds, as a liquid suspension, encapsulated or unencapsulated in liposomes, can be administered to the airways of a patient as an aerosol in a nebulizer, atomizer, or the like to treat respiratory infections. Again, methods for administering liquids to the airways of a patient are also well known in the art.

Gallium nitrate-mediated inhibition of pathogens that are ingested in vivo in animals by phagocytic cells, such as *M. tuberculosis* infection of macrophages, and the like, can be augmented by interferon-γ(IFN-γ). IFN-γ has been found to down regulate macrophage ferritin levels and down regulate expression of transferrin receptors (Byrd, et al. *J. Clin. Invest.* 91:969–976, 1993). Convincing evidence for the ability of IFN-γ to inhibit growth or kill intracellular *M. tuberculosis* alone in human phagocytes is lacking (for example, see Douvas, et al. *Infect. Immun.* 50:1, 1985).

The combination of IFN-γ and gallium nitrate was found to act in concert to reduce growth of *M. tuberculosis* in macrophages (Example 11). While the mechanism is not known, it is likely that IFN-γ decreases the availability of intracellular Fe and gallium nitrate competes effectively for the remaining Fe that the bacterium attempts to scavenge. In these experiments, IFN-γ alone or in combination with gallium nitrate was added to cultures of macrophages infected with *M. tuberculosis.* Initially, 24 h infected macrophages were incubated with various concentrations of IFN-γ alone or in combination with 0 to about 400 μM gallium nitrate. Results, summarized in FIG. 6, demonstrated that IFN-γ augmented gallium nitrate growth inhibition by at least 50%.

Figure 3:
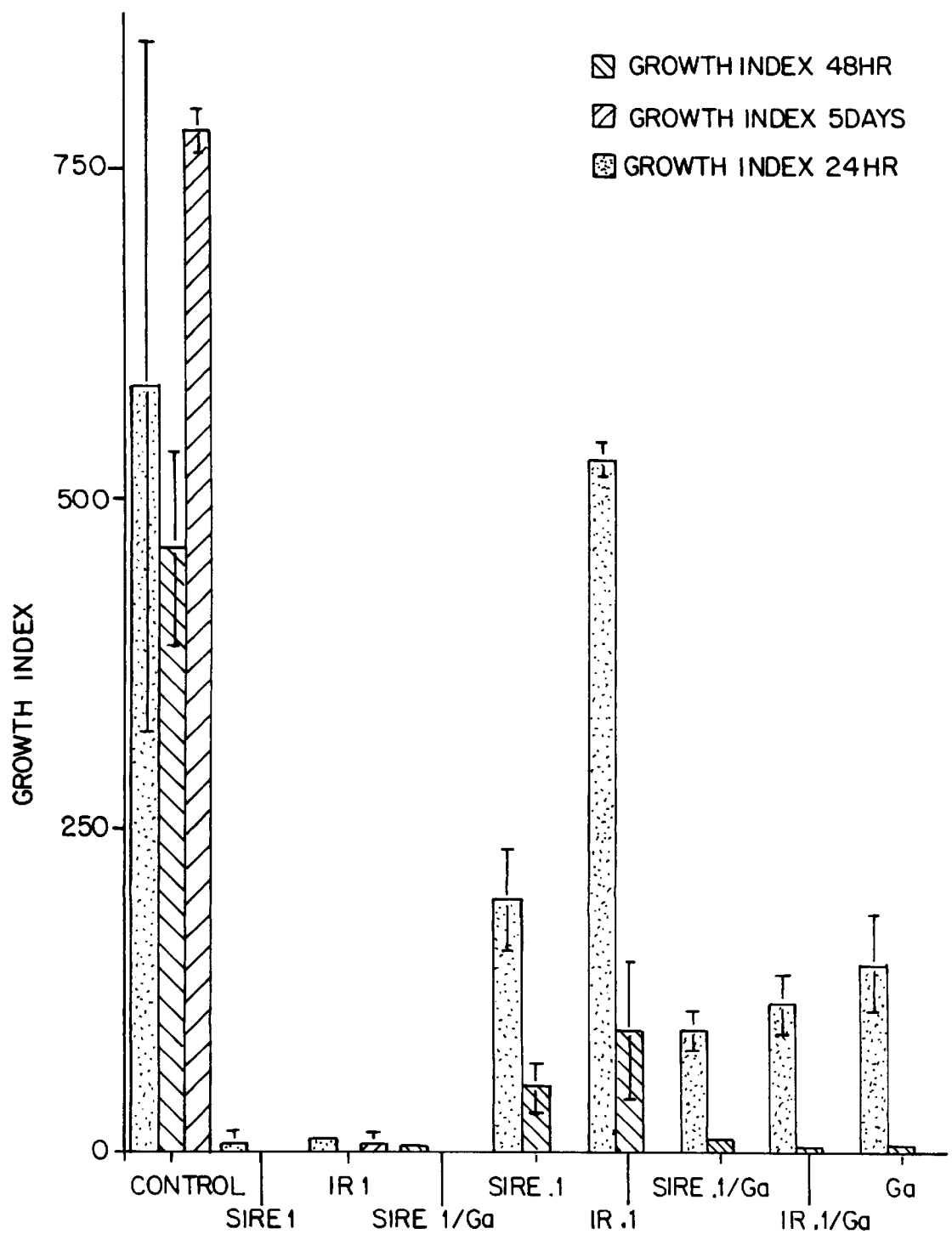
FIG. 3 illustrates results of experiments demonstrating the ability of gallium nitrate to inhibit growth of *M. tuberculosis* in human alveolar macrophages and the augmentation of growth inhabiting when Co.-treated with anti-tuberculous antibiotics.
Figure 4:
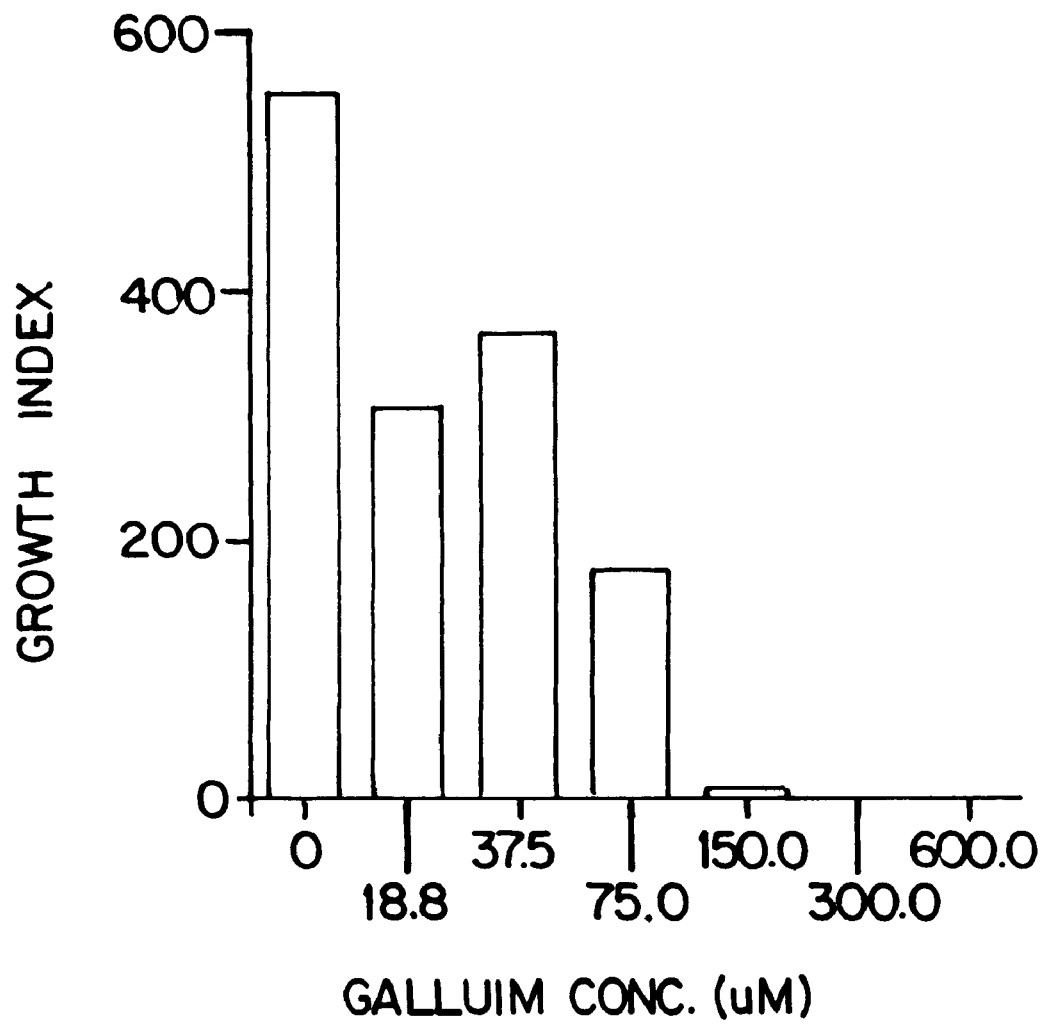
FIG. 4 illustrates results demonstrating the ability of gallium transferrin to inhibit the growth of *M. tuberculosis* strain H37Ra in broth culture.
Figure 5:
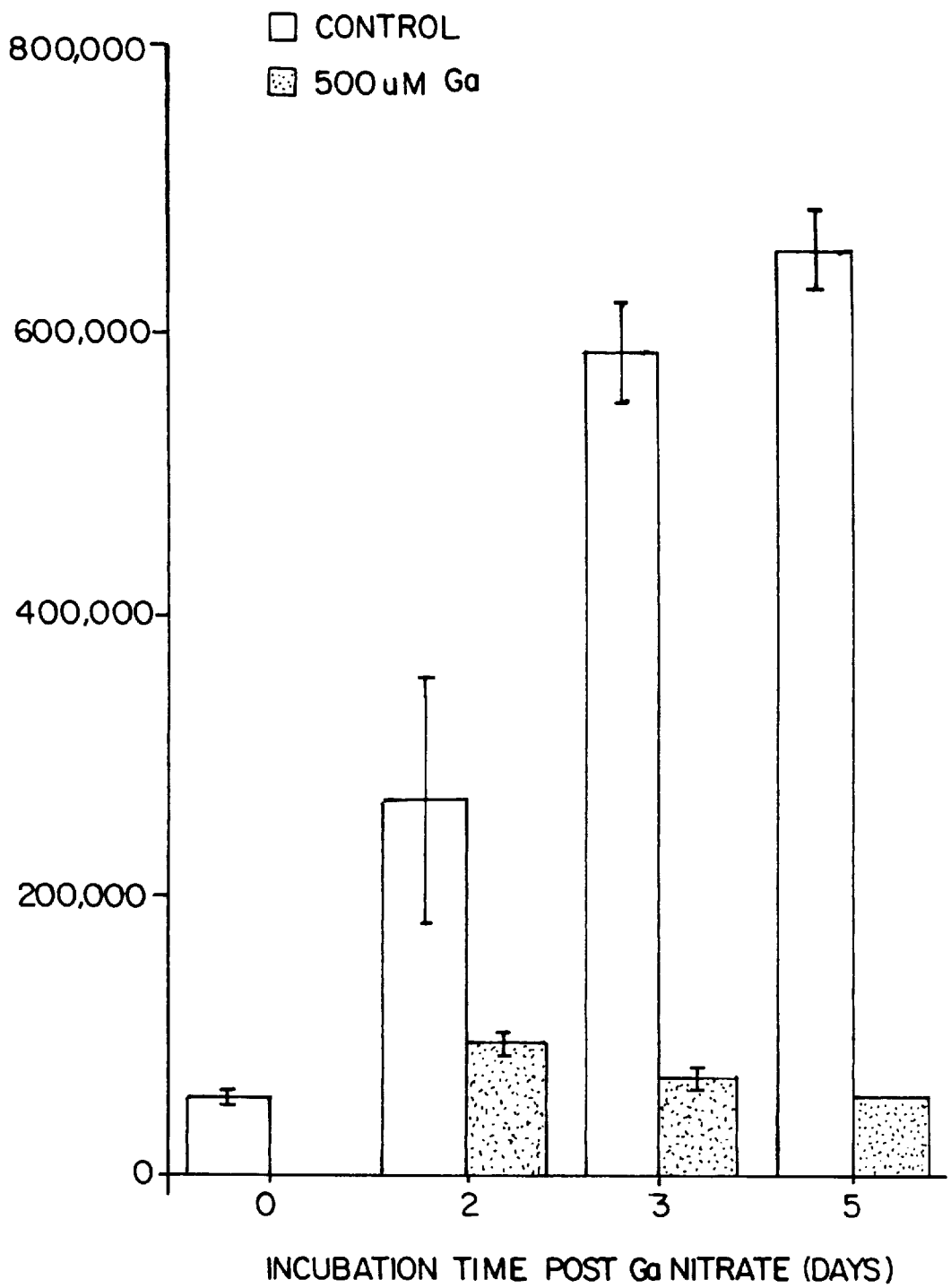
FIG. 5 demonstrates the ability of gallium nitrate to kill *M. tuberculosis* in human macrophages.

Gallium-containing compounds can also be combined with therapies known to inhibit growth of intracellular bacterial pathogens. For example, gallium nitrate was added together with antibiotics known to inhibit *M. tuberculosis* growth (see Example 3 and FIG. 3). Antibiotics known to inhibit *M. tuberculosis* and/or MAI include, but are not limited to, Isoniazid, rifampin, streptomycin, ethambutol, Rifabutin, Clofazimine, Amikacin, Gangamicin, Clarithromycin, and the like. In these studies, *M. tuberculosis*-infected macrophages were incubated with various concentrations of single or multiple antibiotics alone or in combination with gallium nitrate.

Results of combination therapies of antibiotics with gallium nitrate demonstrated enhanced *M. tuberculosis* growth inhibition as compared with antibiotic alone. Referring to Example 3, full doses of the standard first line antibiotics (Isoniazid, rifampin, streptomycin, and ethambutol) were quite potent by 24 h. However, when suboptimal concentrations of streptomycin, isoniazid, rifampin and ethambutol or suboptimal concentrations of Isoniazid and rifampin were used, a clear-cut enhancement in inhibition of *M. tuberculosis* growth by gallium nitrate was seen. Current therapies require the use of anti-mycobacterial antibiotics over a long period of time. Gallium nitrate in conjunction with antibiotics can be used to potentially shorten the anti-mycobacterial therapy time course. The results of these experiments demonstrate that gallium nitrate can be mixed either with a single or with multiple antibiotics including, but not limited to isoniazid, streptomycin, rifampin, ethambutol, pyrazinamide, and the like.

Current antibiotics are less effective in treating strains of *M. tuberculosis* that are multi-drug resistant and patients infected with these strains have increased morbidity and mortality. The term "multi-drug resistant" is used throughout this application to refer to situations where an organism is resistant to treatment by at least two drugs. In the case of Mycobacteria infection, multi-drug resistance refers to resistance to at least two of the first line antibacterials used to treat the organism and generally refers to resistance to at least both isoniazid and rifampin. FIG. 7 and Example 12 summarizes results demonstrating the ability of gallium nitrate to inhibit growth of a mult-drug resistant strain of *M. tuberculosis* that is completely resistant to isoniazid and rifampin (IR) combination therapy. Based on the requirements of intracellular pathogens for iron, gallium nitrate should retain antibacterial activity against even multi-drug resistant strains. Sensitivity of a particular strain of intracellular pathogen to a combined therapy can be tested in vitro using the methods of Examples 3 and 12.

Iron availability is a critical factor for the survival and multiplication of most types of microbial pathogens, particularly intracellular pathogens like *M. tuberculosis* that grow over relatively long periods of time inside cells. Based on the invention disclosed here, other intracellular pathogens will also be susceptible to gallium-containing compounds including gallium nitrate inhibition. These other pathogens include other pathogenic strains of Mycobacteria. To test this theory, two different strains of MAI (a prevalent pathogen in AIDS patients), one obtained from a patient and the other from the ATCC, were separately used to infect macrophages. Gallium nitrate administration resulted in significant inhibition of MAI growth (see Example 13 and FIG. 8).

Other intracellular pathogens including, but not limited to, *Listeria monocytogenes,* Leishmania species (possibly one of the causative agents of Desert Storm Disease), *Histoplasma capsulatum, Legionella pneumophila,* as well as others can be tested in vitro and patients can be treated with gallium-containing compounds using the methods of Example 14 and modifications of these methods known to those skilled in the art.

These studies demonstrate that gallium-containing compounds, such as gallium nitrate, inhibit the growth of a variety of human intracellular pathogens. Importantly and advantageously, as compared with other agents that inhibit *M. tuberculosis* and other intracellular pathogens, resistance to gallium-containing compounds in these pathogens is less likely to occur because iron utilization is an absolute requirement for viability of these organisms. Thus, the development of resistance to gallium nitrate would be infrequent because mutations limiting iron availability to the microbe would result in microbial death (i.e., suicide). This characteristic of gallium-containing compounds is particularly important to the efficacy of these compounds for multidrug resistant strains of *M. tuberculosis.*

The surge in cases of tuberculosis associated with AIDS combined with the increase in *M. tuberculosis* strains resistant to front-line antimycobacterial drugs including rifampin and isoniazid indicate that current options for chemotherpay are inadequate and that new, more effective drugs are needed. These studies, provided herein, demonstrated that the growth of *M. tuberculosis,* including drug resistant strains, and MAI in both broth culture and in human macrophages is markedly reduced in the presence of gallium-containing compounds. Based on the extensive in vivo work related to the use of gallium-containing compounds as antineoplastic agents, it is known that in vivo levels corresponding to effective dosages seen in vitro can be achieved clinically.

Visceral leishmaniasis, the most serious form of human disease cause by Leishmania species, is fatal if untreated. Currently available treatment regimes suffer from both suboptimal efficacy and considerable toxicity. Hence new approaches to therapy are badly needed. *Leishmania chagasi,* the cause of visceral leishmaniasis requires iron for growth and can obtain that iron from human transferrin, lactoferrin and hemin. When incubated in an in vitro culture system (using the culture methods of Wilson et al. *Infect. Immun.* 62:3262–3269, 1994), *L. chagasi* promastigotes were inhibited by the presence of gallium nitrate in a concentration dependent manner with inhibition observed at about at least 500 μM and higher (see Example 14 and FIG. 9).

In another embodiment of this invention, *P. aeruginosa,* the principle cause of chronic lung infections in patients with cystic fibrosis, was also determined to be susceptible to gallium-containing compounds. The PA01 strain of *P. aeruginosa* only grew in an iron-restricted succinate based broth medium (Cox, CD. *Infect. Immun.* 52:263–270, 1986) that included exogenous Ferric chloride or iron chelated to either of the siderophores pyochelin or pyoverdin at concentrations of 1 μM or greater. The addition of gallium nitrate to the iron supplemented medium inhibited *P. aeruginosa* growth (see Example 15). Growth was measure by monitoring the culture medium absorbance at 600 nm.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Assay to Detect Growth Inhibition of *M. tuberculosis* in the Presence of Gallium Nitrate Lyophilized *M. tuberculosis* Erdman strain (ATCC #35801) and H37Ra (ATCC #25177) were reconstituted in pyogen-free water (Sigma, St. Louis, Mo.), plated on 7H11 agar plates, incubated at 37° C. in 5% $CO_2$, 95% air, and after 14 days of culture, harvested and frozen in 7H9 broth at −70° C. Aliquots of frozen stock were thawed, cultured for 9 days on 7H11 agar, scraped from agar plates, resuspended in RPMI-20 mM HEPES (Gibco BRL, Grand Island, N.Y.), and briefly vortexed with two glass beads to break up large clumps. The clumps were allowed to settle over 30 min and the upper bacterial suspension, devoid of clumps, was removed to a second tube. An aliquot of this suspension was diluted in formalin, counted and diluted to appropriate concentrations for use in experiments. $3.0\times10^3$ bacteria/ml *M. tuberculosis* strains H37Ra and Erdman were incubated in BACTEC 12B medium containing 150 μM of ferric Fe salts (Becton Dickinson Diagnostic Instrument Systems, Sparks, Md.) in the absence or presence of various concentrations of gallium nitrate (Alfa Products, Danvers, Mass. and Solopak, Boca Raton, Fla.). Gallium nitrate was prepared in concentrations ranging from between 0 to about 10,000 μM (see FIG. 1A) and between 0 to about 1040 μM gallium nitrate in FIG. 1B. The figures illustrate the recorded numbers from bottles on different days which correlate with growth index readings for the various concentrations of gallium nitrate at Day 6.

The BACTEC system (Becton Dickinson, Sparks, Md.) is an instrument to quantitate bacterial growth. Mycobacteria use a $^{14}C$ labeled fatty acid present in an enriched Middlebrook 7H9 broth. The Mycobacteria release $^{14}CO_2$ into the atmosphere above the medium. During quantitation in the BACTEC instrument, the gas is aspirated from the vial and the $^{14}CO_2$ radioactivity is determined on a scale from 0 to 999. These numbers are designated as the Growth Index (GI). 100GI is approximately equal to 0.025 μCi. The daily increase in the GI is directly proportional to the rate and amount of growth in the medium.

Our studies indicated that growth index readings on days 3 through 10 provides the most sensitive and specific marker of mycobacterial growth (recordings indicated less than or equal to 1000 bacterial particles). These results indicate that gallium nitrate markedly inhibits the growth of *M. tuberculosis* in broth culture, as determined using a radiometric assay with Bactec 12B bottles. The inhibition of growth was dose-dependent with statistically significant inhibition observed at 16.25 μM gallium and marked inhibition at approximately 100 μM gallium.

EXAMPLE 2

Use of Gallium Nitrate to Inhibit Growth of *M. tuberculosis* in Human Monocyte Derived Macrophages (MDM)

Mononuclear phagocytes from healthy adult volunteers who were tuberculin skin test negative and had no history of mycobacterial infection were isolated and cultured in Teflon wells according to the methods of Schlesinger, et al. (*J. Immunol.* 150:2920–2930, 1993). After 5 days, the cells were removed and the MDM population was adhered to wells of a 24 well tissue culture plate. In certain wells, monolayers were allowed to form on glass coverslips to assess the mean number of bacteria per macrophage at different time points. Monolayers thus formed were incubated for an additional week in the presence of 20% autologous human serum to ensure maintenance of the monolayer after incubation with *M. tuberculosis.* Macrophage monolayers were incubated with single suspensions of *M. tuberculosis* strains (H37Ra and Erdman) using methods disclosed by Schlesinger, L S, et al. (*J. Immunol* 144:2771–2780, 1990). Macrophages were infected at a bacteria: macrophage ratio of about 1:1 to about 1:5. Incubations of bacteria with macrophages were performed in the absence of serum. After a 2 h incubation, bacteria was washed away and monolayers were incubated with RPMI medium containing 1% autologous serum. Various concentrations of gallium nitrate were added 24 h after initial infection in the ranges of about 1 to about 1000 μM gallium. Supernatants and monolayer lysates were harvested 24, 48 and 72 h after gallium administration.

Gallium nitrate caused a dose-dependent inhibition of growth of both virulent and attenuated strains of *M. tuberculosis* in human macrophages. Inhibition of growth was observed even after 24 h of gallium nitrate administration to infected macrophages. More marked inhibition of growth was observed at 48 and 72 h post gallium addition. Results are provided in FIG. 2. In subsequent experiments, infected monolayers were allowed to continue growing in the presence of gallium for as long as the monolayer integrity remained intact. These studies were performed to determine if longer incubation periods resulted in greater bacterial inhibition. Cell monolayers were lysed in sodium dodecyl sulphate (SDS) and neutralized in BSA in medium containing 7H9 broth (BBL Microbiology Systems, Bectin Dickinson, Sparks, Md.). Supernatants and monolayer lysates were centrifuged to pellet bacteria. The medium was carefully removed, the pellet was resuspended in 200 μl of 7H9 broth and the broth was inoculated directly into BACTEC 12B bottles for assessment of growth using the radiometric system. Results indicated that the administration of gallium nitrate significantly inhibited growth of *M. tuberculosis* in human macrophages.

EXAMPLE 3

Gallium Nitrate Inhibition of *M. tuberculosis* in Human Alveolar Macrophages Augments the Growth Inhibition of Anti-tuberculous Antibiotics Human alveolar macrophages were purified from healthy non-smoking adult volunteers and placed in monolayer culture. *M. tuberculosis* infected cells were treated with gallium nitrate as described in Example 2. Antituberculous antibiotics were added to wells alone or with gallium nitrate at 500 μM 24 h after *M. tuberculosis* infection. Antituberculous antibiotics tested included streptomycin (2.016 μg/ml), isoniazid (0.1 μg/ml), rifampin (2.0 μg/ml), and ethambutol (2.52 μg/ml) and the combination of antibiotics was denoted as SIRE. Antibiotics were obtained in lyophilized form from BACTEC. The antibiotics were reconstituted in sterile water per package instructions. With reference to FIG. 3, SIRE refers to combinations of streptomycin, isoniazid, rifampin and ethambutol while IR refers to combinations of Isoniazid and rifampin.

Infected macrophages were cultured for 24 h, 48 h, or 120 h. Growth index readings of combined supernatants and cell lysates were measured in the BACTEC 460 TB system. Results are provided in FIG. 3 and indicated that gallium nitrate augments the ability of suboptimal concentrations of antibiotics (1/10 the standard concentrations) to inhibit *M.tuberculosis* growth. Since these antibiotics have a number of unpleasant side effects that are reduced at reduced concentrations of the drugs, combined therapies that permit these antibiotics to be administered at lower doses when combined with gallium nitrate is significant and may help to promote better drug compliance in patients infected with *M. tuberculosis.*

EXAMPLE 4

Methods to Determine whether Gallium Nitrate Killed *M. tuberculosis*

In Examples 2 and 3, gallium nitrate inhibited growth of *M. tuberculosis.* To determine whether the mycobacteria strains were killed by gallium nitrate or whether various concentrations of gallium nitrate were bacteriostatic, samples from the assay were tested in the BACTEC system. Media from test samples demonstrating no mycobacteria growth over time were removed for testing and the mycobacteria was pelleted by centrifugation (10,000×g). The bacteria, if present, was resuspended in 7H9 broth without gallium nitrate and incubated in the BACTEC system under conditions known in the art to promote bacterial growth. The growth index for the cultures were assessed according to the methods of Example 1 and results indicated that bacteria did not grow in the BACTEC system following gallium nitrate treatment.

EXAMPLE 5

Colony-Forming Unit Assay to Assess Pathogen Death

The growth index assay cannot always clearly distinguish between bacterial survival (without multiplication) and bacterial death. Therefore, colony forming unit assays were also used to assess the bactericidal activity of gallium-containing compounds in these experiments. Lysed monolayers were plated in Middlebrook 7H11 plates and colonies forming on the plates were counted after 14 days. Between days 2 and 5 following gallium nitrate administration, there was a continuous decrease in colony-forming units from macrophage lysates providing evidence for actual bacterial killing by gallium nitrate (FIG. 5). At day 5, the actual colony-forming units fell only slightly below the initial amount of bacteria in macrophages. This result was observed because the assay had to be terminated at day 5 because infected macrophages not exposed to gallium nitrate were being lost. In fact, this experiment provided the most graphic illustration of the influence of gallium nitrate on bacterial killing. That is, control-infected monolayers were lysed as a result of bacterial multiplication so that macrophages could no longer be visualized by microscopy. In contrast, gallium nitrate-treated macrophages maintained a very good monolayer during the course of the assay. Importantly, the results in the colony-forming unit assay resemble the results obtained with the radiometric BACTEC assay.

EXAMPLE 6

The Use of Gallium Transferrin to Inhibit *M. tuberculosis*

Duplicate studies were performed using gallium transferrin to study the effect of gallium in a form that would be available to *M. tuberculosis* in vivo. Human apotransferrin (Sigma Chemicals, St. Louis, Mo.) was mixed 1:1 (by molar ratio) with gallium. Gallium concentrations ranged from 0 to about 600 μM. Growth index readings on Day 10 are provided in FIG. 4. Marked inhibition of growth was seen at a lower concentration of gallium (75 μM) than was observed when gallium nitrate was used (100 μM) as shown in FIG. 4. The control cultures were treated with transferrin alone and no inhibition in bacterial growth was observed. The results employing gallium transferrin support the finding that gallium is useful in vivo for inhibiting growth of *M. tuberculosis.* This experiment was important because the administration of gallium nitrate in the bloodstream will likely result in the transfer of gallium to transferrin with presentation of gallium in the form of gallium transferrin to macrophages.

EXAMPLE 7

Gallium Toxicity Studies in Uninfected Cells

To test the potential toxicity of gallium nitrate on the standard macrophage monolayers (MDMs) used in the assays described in this invention, uninfected MDM monolayers were incubated with various concentrations of gallium nitrate in the range used in the studies described in Examples 2 and 3.

There was no immediate difference in monolayer density between MDM monolayers with and without gallium nitrate treatment up to a gallium concentration of 2 mM. Results were based on counting napthol blue macrophage stained nuclei from the monolayer. These numbers directly correlate with the number of cells present. In most cases the integrity of the MDM monolayer in the presence of gallium was maintained for up to 37 days, equivalent to untreated, uninfected control cultures.

EXAMPLE 8

Monolayer Density of Macrophages (MDMs) Infected with *M. tuberculosis* and Treated with Gallium Nitrate Macrophages were infected with *M. tuberculosis* at a ratio of 1:5 (MDMs:bacteria) and treated with 500 μM or 1 mM gallium nitrate. Cell density was assessed over time. The results of the experiments comparing the monolayer integrity of untreated vs. gallium nitrate treated cultures were as follows:

Experiment No. 1

| Day | Time postinfection | Monolayer Integrity |
| --- | --- | --- |
| 1 | 24 h. | No difference |
| 8 | 9 days | 25–50% more cells in Ga-treated cultures |
| 11 | 12 days | 4–5 times as many cells in Ga-treated cultures |
| 29 | 30 days | 4–5 times as many cells in Ga-treated cultures |
| 33 | 34 days | No difference between monolayers treated with Ga-nitrate. Control wells containing *M. tuberculosis* had no cells left. |

| | | Experiment #2 |
|---|---|---|
| Day | Time postinfection | Monolayer Integrity |
| 1 | 24 hr. | No difference between Ga-treated and control |
| 3 | 4 days | No difference between Ga-treated and control |
| 6 | 7 days | 2–4 times the number of cells in Ga-treated cultures |
| 8 | 9 days | No cells left on control monolayer 40%–50% of the original number of cells on Ga treated monolayers. |

EXAMPLE 9

Animal Studies

Four week old female inbred CD-1 mice are infected intravenously through a caudal vein with the Erdman strain of M. tuberculosis. M. tuberculosis bacteria are grown in modified Middlebrook 7H10 broth (Difco Laboratories, Detroit, Mich.). The organism is grown in modified 7H10 broth with 10% OADC enrichment and 0.05% Tween 80 on a rotary shaker for 5 days. The culture suspension is diluted in broth to yield 100 Klett units/ml (Klett-Summerson colorimeter, Klett Manufacturing Brooklyn N.Y.) or about $5 \times 10^7$ CFU/ml. The size of the inoculum is determined by titration and counting from triplicate 7H10 agar plates (BBL Microbiology Systems, Cockeysville, Md.) supplemented with 10% OADC enrichment (oleic acid-albumin-dextrose-catalase). The plates are incubated at 37° C. for 4 weeks prior to counting.

Each mouse receives about $10^7$ viable organisms suspended in 0.2 ml. of modified 7H10 broth with 8–10 mice per group. Treatment begins 1 week post infection. A control group of infected mice (early controls) are sacrificed at the start of treatment. Treatment is given as a single dose of IV gallium, preferably as gallium nitrate, as a continuous dose over 5–7 days or given 2–3 weekly doses. Remaining animals in a control group of infected but untreated mice (late controls) are sacrificed at the end of the treatment period. Doses of compound tested include 50/mg/kg for intravenous administration, 50 mg/kg per intraperitoneal administration and 50 mg/kg for subcutaneous administrations. Animals are sacrificed 3–5 days after the last dose of drug. Spleens and lungs are aseptically removed and ground in a tissue homogenizer. The number of viable organisms are determined by titration on 7H20 agar plates according to the methods of Example 5 and Klemens et al.(Antimicrob. Agents and chemotherpay. 38:2245–48, 1994).

Those skilled in the art will recognize that organisms can be administered to experimental animals intraperitoneally, intravenously, by aerosol or by alternative routes.

In this example, animals are infected by aerosol (Pal et al. Infection and Immunity 60:4781–4792, 1992). When guinea pigs are exposed to low numbers of aerosolized M. tuberculosis cells they consistently develop a pulmonary infection that both clinically and pathologically resembles tuberculosis in humans. In these experiments, lyophilized bacteria are reconstituted in Middlebrook 7H9 media and maintained on 7H11 agar at 37° C. After culture for 7 days, organisms are scraped from the plates, suspended in 7H9 broth and frozen. Guinea pigs weighing 300 to 400 g at the start of the experiment can be used. The animals are infected by aerosol. M. tuberculosis is thawed and cultured on Middlebrook 7H11 agar for 7 days, scraped from the plates and a suspension containing single bacilli is prepared by transferring 2 loopfulls of organisms to a Sarstedt tube (Sarstedt, Inc. Princeton JF) containing 2–3 mm glass beads in 1 ml of 7H9 culture media. The cells are pulsed vigorously to break up clumps. Remaining clumps are allowed to settle for 30 min. and a 100 µl aliquot is removed. The cell concentration in the suspension is determined by counting in a Petroff Hausser chamber (Hausser Scientific Partnership, Horsham, Pa.). Guinea pigs are exposed to aerosols of viable M. tuberculosis in a specially designed lucite aerosol chamber according to Challu, et al. Indian J. Tuberc. 36:107–11, 1989 and Pal, et al. (supra). Animals are exposed to aerosols for 30 min. during which time the suspension of bacilli in the nebulizer is completely exhausted. Following infection, animals are treated with gallium-containing compound doses ranging from about 200 mg/m$^2$/day to about 750 mg/m$^2$/day delivered by aerosol or in other experiments by intravenous administration or other routes known to those skilled in the art. At various times after infection the animals are sacrificed and lung and spleen homogenates are tested for viable organisms using the colony forming assay of Example 5. Reduced colonies on the plates treated with gallium nitrate is evidence of in vivo efficacy.

Gallium-containing compounds can be given to an experimental animal by a variety of administration routes known in the art, including, but not limited to, aerosol, oral, intravenous, intraperitoneal routes, subcutaneous administration, and the like.

EXAMPLE 10

Human Clinical Testing

From studies designed to treat cancer patients, it is known that healthy patients can tolerate at least about 200 mg/m$^2$/day gallium nitrate for at least 7 days and generate steady state gallium concentrations of 1.0 to 1.5 mg/L using intravenous administration (Todd, et al. Drugs 42(2):261–273, 1991). Toxicological studies for the treatment of gallium nitrate in cancer patients have treated human subjects with a single dose every 2–3 weeks of about 700 mg/m$^2$/day to about 750 mg/m$^2$/day; or daily administration for three days every two weeks at about 300 mg/m$^2$/day; or a seven day continuous infusion every 3 to 5 weeks of about 300 mg/m$^2$/day. To assess the ability of gallium-containing compounds to treat tuberculosis, patients with active tuberculosis are randomized to either: 1) a standard antibiotic regime alone; 2) Gallium-containing compound treatment alone administered IV, orally, subcutaneous or by aerosol in a range of concentrations demonstrated to be safe (see Todd, et al.) over about a 5–7 day period; and 3) antibiotics plus gallium-containing compound. Alternatively, those skilled in the art will recognize that one can look at suboptimal doses of antibiotics with concentrations of the gallium-containing compounds.

The patients are assessed weekly for 1) clinical signs and symptoms of tuberculosis including for example, fever, weight loss, night sweats, cough, and chest pain; 2) changes in chest X-ray over time, 3) sputum sample for cultures and AFB smear; as well as 4) renal function, liver function tests, complete blood count and hearing problems (resulting primarily because of antituberculosis drugs). Other clinical experiments to assess the growth inhibitory capacity of other gallium-containing compounds for M. tuberculosis or other intracellular pathogens can be readily designed without undue experimentation by those skilled in the art.

EXAMPLE 11

The Ability of Gallium Nitrate to Augment the Ability of Interferon-γ (IFN-γ) to Inhibit the Growth of M. tuberculosis in Macrophages.

Figure 6:
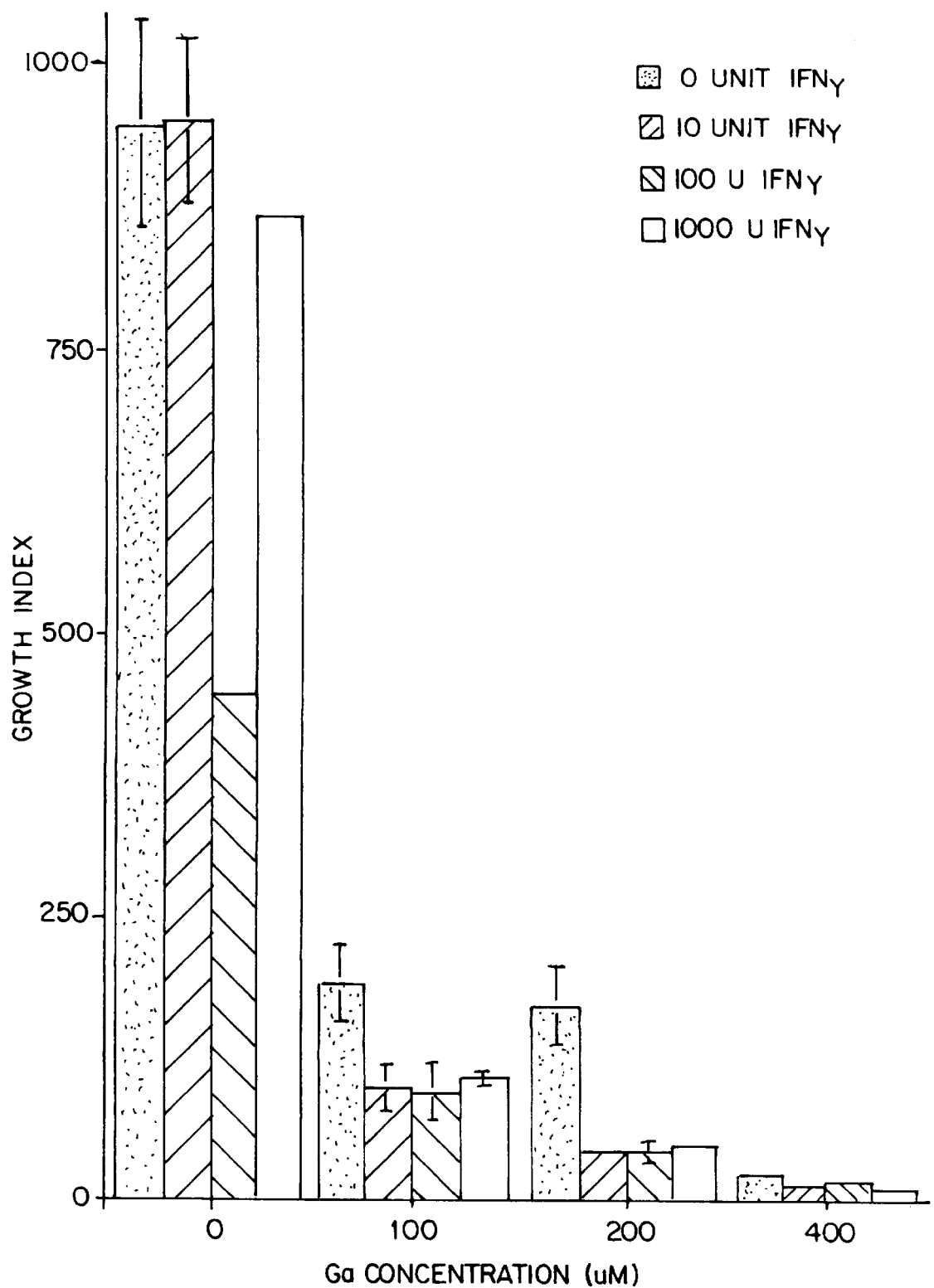
FIG. 6 is a graph demonstrating the ability of interferon-γ to augment the growth inhibition of *M. tuberculosis* in macrophages with gallium nitrate.

The administration of interferon-γ augments the inhibition of growth of M. tuberculosis in macrophages seen with gallium nitrate (see FIG. 6). The cytokine, interferon-γ, was found to decrease iron availability in macrophages by decreasing macrophage ferritin levels and by decreasing expression of transferrin receptors. These experiments determined whether the effect of gallium nitrate was augmented under conditions in which iron availability was reduced. Human interferon-γ (0–1000U, Genzyme, Cambridge, Mass.) was added to macrophage monolayers for 20 hrs prior to adding *M. tuberculosis*. Gallium nitrate was added 24 h. after *M. tuberculosis* infection. The results indicated that interferon-γ in various concentrations augmented the growth inhibition seen with gallium nitrate by approximately 50% or more at 100 μM.

EXAMPLE 12

Inhibition of Multi-drug Resistant Strain of *M. tuberculosis* Using Gallium Nitrate A patient isolate of MDR-TB (resistant to isoniazid and rifampin) was obtained from the state hygienic laboratory at the University of Iowa. The experiment was performed exactly as provided in Example 3. Gallium concentrations tested ranged from about 0 μM to about 500 μM in combinations with isoniazid and rifampin (IR) dosages that ranged from about 0 to about 1.0 dose of IR (one dose of IR equaling a dose having 0.1 μg/ml isoniazid and 2.0 μg/ml rifampin). As predicted, standard doses of IR had no activity against this *M. tuberculosis* strain. In contrast, gallium nitrate retained full activity against this strain. Results of this experiment are illustrated in FIG. 7. Thus, gallium nitrate should serve as a potent therapy for MDR strains of *M. tuberculosis*.

EXAMPLE 13

Gallium Nitrate Inhibits the Growth of *M. avium-intracellulare* Complex in Human Alveolar Macrophages.

Figure 8A:
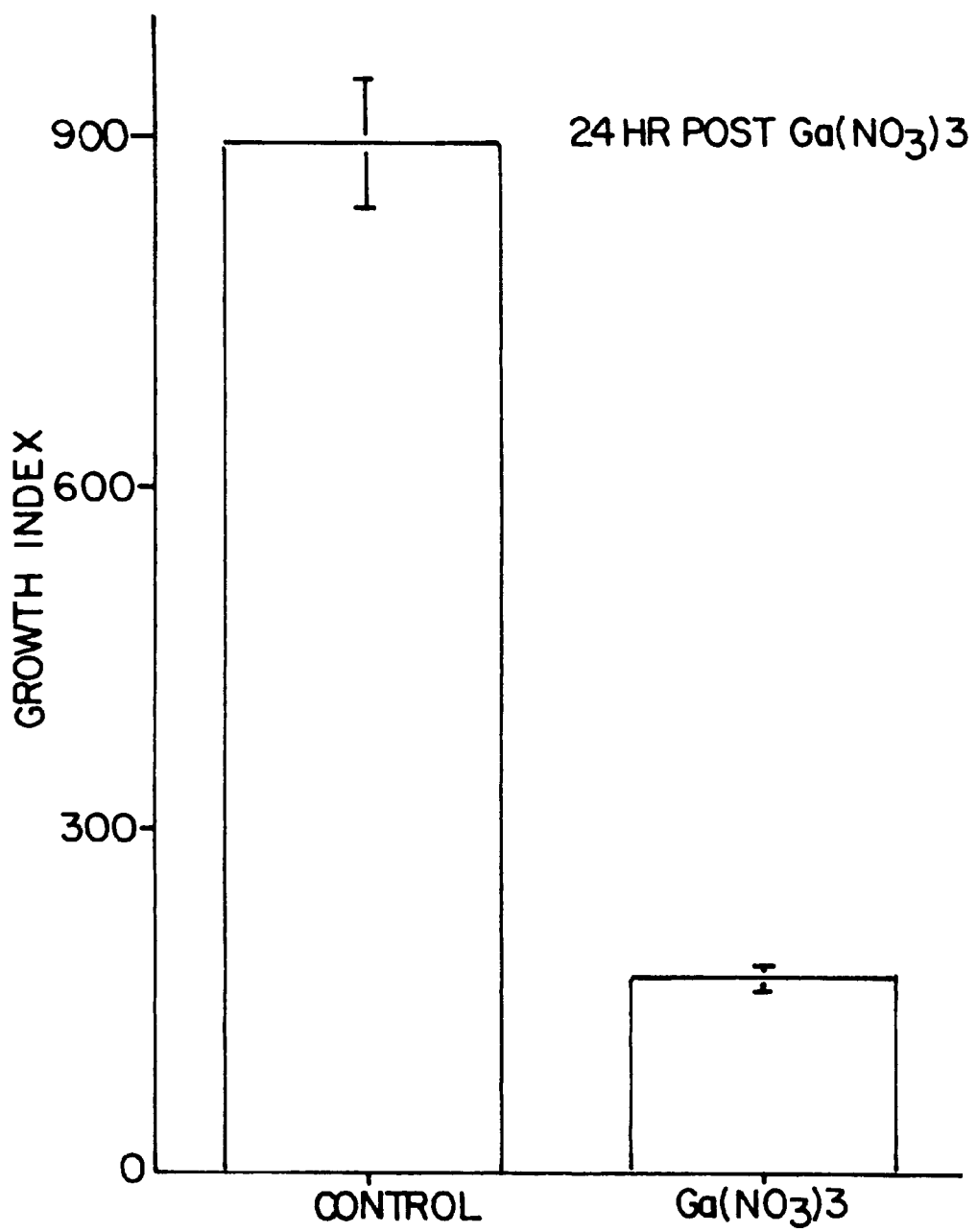
FIG. 8A demonstrates growth inhibition in a commercially-available MAI isolate and FIG. 8B demonstrates growth inhibition in a patient MAI isolate.
Figure 8B:
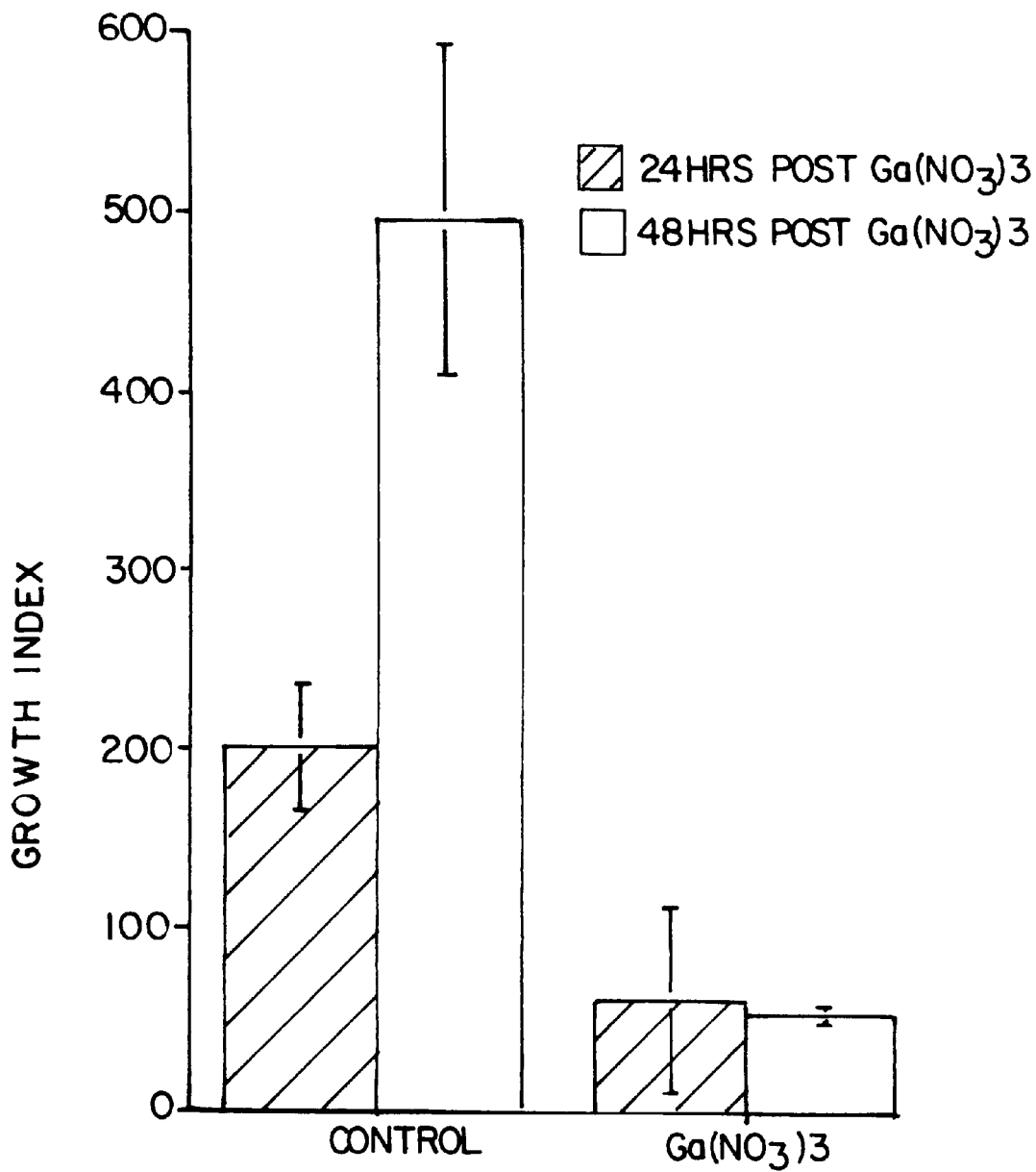
FIG. 8 illustrates results of experiments demonstrating the ability of gallium nitrate to inhibit the growth of MAI in human alveolar macrophages.

*M. avium-intracellulare* complex (MAI) was obtained from the ATCC (#25291) and from a patient isolate from the State Hygienic laboratory at the University of Iowa Hospital and Clinics. Human alveolar macrophages were obtained from broncholavage of healthy patients and placed in monolayer culture. The bacteria were added to the cells in a bacteria to macrophage ratio of about 1:1. Growth index readings were obtained at 24 hr and 48 hr after gallium nitrate administration (500 μM) as described in Example 3 and used by Cavalieri, et al. (*Antimicrob. Agents and Chemo.* 39:1542–1545, 1995). Results are provided in FIG. 8 and indicated that gallium nitrate inhibits the growth of MAI.

EXAMPLE 14

Gallium Nitrate Inhibition of *Legionella pneumophila*, *Leishmania chagasi* and *Histoplasma capsulatum*

Amastigotes were isolated from the spleens of infected hamsters and allowed to convert to promastigotes by cultivation in a modified minimal essential medium (HOMEM) with 10% heat inactivated fetal calf serum and hemin (8 μM). Parasites were used within 21 days of isolation from an infected hamster. Promastigote cultures were seeded at $10^6$ promastigotes per ml and used after 2 to 3 days in logarithmic phase or 5 to 7 days in stationary phase of growth. During growth studies with gallium nitrate, promastigotes were suspended in iron-containing HOMEM to allow for organism growth. To assess the effect of gallium nitrate on promastigote growth, gallium nitrate was added at concentrations ranging from about 250 μM to about 2 mM for about 24 to about 120 hrs. As illustrated in FIG. 9, *Leishmania chagasi* promastigotes were significantly inhibited by gallium nitrate.

Labeled *Leishmania chagasi* promastigotes are added to macrophage monolayers (ratios of about 1:1 to about 1:10 macrophages to promastigote, incubated for 45 min at 36° C.) and the number of intracellular organisms is determined at about 24 to about 120 h after gallium addition (versus control monolayers) according to the methods of Mosser et al. and/or Wilson et al. (*Nature* 327:329–331, 1987 and *J. Immunol* 144:4825–4834,1990). The number of organisms associated with the monolayer at one hour after infection is determined using a parasite radiobinding assay that measures the total number of macrophage-associated organisms or assessed by staining the monolayer and counting the number of organisms per macrophage using light microscopy.

Peripheral blood mononuclear cells (PBMC) are isolated from blood of human donors without a history of histoplasmosis by density gradient centrifugation. The PBMC are washed in RPMI-1640, adjusted to $5 \times 10^6$ cells/ml in complete tissue culture medium (10% autologous serum, RPMI-1640 with antibiotics). The cells are dispensed into eight-chamber Lab-Tek chamber slides (Nunc Inc., Naperville, Ill.) and incubated for 2 h at 37° C. in 5% $CO_2$ and air. The non-adherent cells are removed and the cells were washed. The cells are incubated with 0.25 ml. of *H. capsulatum* suspension as described by Desai, et al. *J. Med. Microbiol.* 43:224–229, 1995. The cells are incubated for 3 h. at 37 ° C. and the non-adherent *H. capsulatum* cells are aspirated and the monolayer is washed. The aspirate with rinse material is cultured to determine the number of non-adherent fungal units. Cultures are treated with a gallium-containing compound, preferably gallium nitrate, at concentrations ranging from 10 μM to 1000 μM. Following treatment, macrophage monolayers with ingested or adherent cells are harvested with five washes of sterile water to lyse the macrophages. Different dilutions of harvested material are plated onto S-BHI agar plates (supplemented brain heart infusion agar plates, 445 ml BHI agar with 50 ml 1% bovine serum albumin). The plates are dried for 1 day at 35° C. and then incubated at 37° C. for 5 days. The number of cfu/plate is counted and the number of cfu/culture is calculated. The percentage killing is determined using the formula [1-(cfu from experimental culture/cfu from inoculum)]×100.

For assessing gallium-containing compound-mediated inhibition of *Legionella pneumophila* infection, PBMC are obtained as described above. Culture macrophages are incubated with a virulent strain of *L. pneumophila* obtained from a patient isolate (or other isolates obtained from ATCC) and cultured on buffered charcoal yeast extract medium (GIBCO Laboratories, Madison Wis.) as described (Yamamoto, Y. et al., *Curr. Microbiol.* 16:333–336, 1988). Approximately $1 \times 10^6$ macrophages are incubated at a multiplicity of infection of about 1:1 to about 1:10 macrophages:organism. Cultures are incubated for 30 min at 37 ° C. and washed with HBSS to remove nonphagocytosed bacteria. Cells are incubated for various time periods at 37° C. in RPMI 1640 with 15% fetal calf serum in the presence of concentrations of gallium nitrate varying from about 10 μM to about 1000 μM. Following culture, the cells are lysed in water and quantitated as described by Yamamoto, et al. (*Infection and Immunity* 60:3231–3237, 1992).

EXAMPLE 15

Gallium Nitrate Inhibition of *P. aeruginosa*

*P. aeruginosa* strain PA01 was suspended in succinate-based medium (Cox, C. D., *Infect. Immun.* 52:262–270, 1986) to an optical density of approximately 0.040 at 600 nm in the absence (negative control) or presence of 1 $\mu$M ferric chloride (positive growth control). To some aliquots of both positive and negative control conditions, gallium nitrate was added at varying concentrations. The bacterial suspensions were placed at 37° C. for 7 h and growth was determined by measuring absorbance at 600 nm. Over the time of incubation, minimal growth was observed in the non-ferric chloride supplemented bacterial suspension (A600=0.072). With the inclusion of ferric chloride the concentration of organisms increased nearly eight fold A600=0.297). Significant inhibition of *P. aeruginosa* growth was observed with the addition of 100 $\mu$M and 10 $\mu$M of gallium nitrate in the ferric chloride supplemented conditions. Growth was completely inhibited at 100 $\mu$M (A600=0.043) and decreased by more than 50% (A600=0.130) at 10 $\mu$M gallium nitrate. Slight inhibition was observed at 1 $\mu$M gallium nitrate (A600=0.270).

While particular embodiments of the invention have been described in detail, it will be apparent to those skilled in the art that these embodiments are exemplary rather than limiting, and the true scope of the invention is that defined in the following claims.

What is claimed is:

1. A method for inhibiting growth of an intracellular pathogen comprising delivering a therapeutically effective dose of a gallium-containing compound in a pharmaceutically acceptable buffer to a mammal having cells infected with an intracellular pathogen as a result of phagocytosis.

2. The method of claim 1 wherein the cells are mononuclear phagocytes.

3. The method of claim 1 wherein the method also includes treating the mammal with at least a second compound that has activity to inhibit the growth of an intracellular pathogen.

4. The method of claim 3 wherein the second compound is an antibiotic.

5. The method of claim 4 wherein the antibiotic is selected from the group consisting of streptomycin, isoniazid, rifampin, pyrazinamide and ethambutol.

6. The method of claim 1 wherein the pathogen is a member of the genus Mycobacteria.

7. The method of claim 6, wherein the pathogen is a multi-drug resistant strain of the genus Mycobacteria.

8. The method of claim 1, wherein the therapeutically effective dose is at least 50 mg/m$^2$/day.

9. The method of claim 1 wherein delivering comprises delivering the therapeutically effective dose to a human patient having cells infected with an intracellular pathogen.

10. The method of claim, wherein the cells are mononuclear phagocytes.

11. The method of claim 9, wherein the therapeutic effective dose is delivered intravenously.

12. The method of claim 9, wherein the therapeutic effective dose is delivered by aerosol.

13. The method of claim 9, wherein the therapeutic effective dose is delivered orally.

14. The method of claim 1, additionally comprising combining the gallium-containing compound with liposomes before the delivering step.

15. The method of claim 1, additionally comprising delivering interferon-$\gamma$ to the mammal.

16. The method of claim 1, wherein the gallium-containing compound is gallium nitrate.

17. A method for inhibiting growth of an intracellular pathogen comprising delivering a therapeutically effective dose of a gallium-containing compound in a pharmaceutically acceptable buffer to a mammal having cells infected with an intracellular pathogen as a result of phagocytosis, wherein the pathogen is selected from the group consisting of Legionella, Histoplasma, and Leishmania.

18. A method for inhibiting growth of an intracellular pathogen comprising delivering a therapeutically effective dose of a gallium-containing compound in a pharmaceutically acceptable buffer to a mammal having cells infected with an intracellular pathogen as a result of phagocytosis, wherein the pathogen is *Mycobacterium tuberculosis*.

* * * * *

UNITED STATES PATENT AND TRADEMARK OFFICE
CERTIFICATE OF CORRECTION

PATENT NO. : 6,203,822 B1
DATED : March 20, 2001
INVENTOR(S) : Larry S. Schlesinger et al.

It is certified that error appears in the above-identified patent and that said Letters Patent is hereby corrected as shown below:

Column 4,
Line 12, delete "inhabiting" and insert -- inhibition -- therefor.
Line 12, delete "Co." and insert -- co -- therefor.

Column 6,
Line 2, delete "Mor et al. (*Antimicrobial*" and insert -- (Mor et al., *Antimicrobial* -- therefor.

Column 9,
Line 22, delete "*Inf and Inm.*" and insert -- *Inf. and Imm.* -- therefor.

Column 10,
Line 30, delete "10:1 130" and insert -- 10:1130 -- therefor.

Column 22, claim 10,
Line 13, insert -- 9 -- after "The method of claim".

Signed and Sealed this

Twenty-second Day of January, 2002

Attest:

JAMES E. ROGAN
Attesting Officer
Director of the United States Patent and Trademark Office